(12) United States Patent
Bhatt et al.

(10) Patent No.: US 10,112,988 B2
(45) Date of Patent: Oct. 30, 2018

(54) METHODS OF ASSESSING AMYLOID-BETA PEPTIDES IN THE CENTRAL NERVOUS SYSTEM BY BLOOD-BRAIN BARRIER PERMEABLE PEPTIDE COMPOSITIONS COMPRISING A VAB DOMAIN OF A CAMELID SINGLE DOMAIN HEAVY CHAIN ANTIBODY AGAINST AN ANTI-AMYLOID-BETA PEPTIDE

(71) Applicant: ICB International, Inc., La Jolla, CA (US)

(72) Inventors: Ram S. Bhatt, San Diego, CA (US); Rishi Bhatt, San Diego, CA (US)

(73) Assignee: ICB INTERNATIONAL, INC., La Jolla, CA (US)

( * ) Notice: Subject to any disclaimer, the term of this patent is extended or adjusted under 35 U.S.C. 154(b) by 51 days.

(21) Appl. No.: 13/917,010

(22) Filed: Jun. 13, 2013

(65) Prior Publication Data

US 2014/0193834 A1    Jul. 10, 2014

Related U.S. Application Data

(63) Continuation-in-part of application No. 13/736,852, filed on Jan. 8, 2013.

(60) Provisional application No. 61/631,731, filed on Jan. 9, 2012.

(51) Int. Cl.
| | | |
|---|---|---|
| *A61K 49/00* | (2006.01) | |
| *A61K 39/395* | (2006.01) | |
| *A61K 39/00* | (2006.01) | |
| *G01N 33/53* | (2006.01) | |
| *A61K 49/16* | (2006.01) | |
| *G01N 33/567* | (2006.01) | |
| *A61K 38/00* | (2006.01) | |
| *C07K 14/00* | (2006.01) | |
| *C07K 16/00* | (2006.01) | |
| *C12P 21/08* | (2006.01) | |
| *A61B 5/00* | (2006.01) | |
| *C07K 16/18* | (2006.01) | |
| *G01N 33/68* | (2006.01) | |
| *A61K 47/48* | (2006.01) | |

(52) U.S. Cl.
CPC ............ *C07K 16/18* (2013.01); *A61K 47/489* (2013.01); *A61K 47/48538* (2013.01); *G01N 33/6857* (2013.01); *G01N 33/6896* (2013.01); *A61K 38/00* (2013.01); *C07K 2317/22* (2013.01); *C07K 2317/34* (2013.01); *C07K 2317/569* (2013.01); *C07K 2317/64* (2013.01)

(58) Field of Classification Search
CPC ........ A61K 2039/505; A61K 47/48538; A61K 47/48415; A61K 2039/54; A61K 38/00; A61K 47/489; A61K 9/0085; A61K 47/48192; C07K 2317/24; C07K 2317/56; C07K 2317/569; C07K 2317/22; C07K 16/18; C07K 2317/565; C07K 2317/76; C07K 2317/92; C07K 16/00; C07K 2317/34; C07K 2317/21; C07K 2317/567; C07K 2317/64; G01N 33/6857; G01N 33/6896; A61M 5/28; C12Q 1/68
See application file for complete search history.

(56) References Cited

U.S. PATENT DOCUMENTS

| | | | |
|---|---|---|---|
| 5,759,808 A | 6/1998 | Casterman et al. | |
| 5,800,988 A | 9/1998 | Casterman et al. | |
| 5,817,765 A | 10/1998 | Isaksson et al. | |
| 5,840,526 A | 11/1998 | Casterman et al. | |
| 5,874,541 A | 2/1999 | Casterman et al. | |
| 6,005,079 A | 12/1999 | Casterman et al. | |
| 6,010,961 A | 1/2000 | Blume | |
| 6,015,695 A | 1/2000 | Casterman et al. | |
| 6,765,087 B1 | 7/2004 | Casterman et al. | |
| 6,838,254 B1 | 1/2005 | Hamers et al. | |
| 7,371,849 B2 | 5/2008 | Honda et al. | |
| 7,977,071 B2 * | 7/2011 | Nuttal ................. | C07K 14/461 424/133.1 |
| 8,414,893 B2 * | 4/2013 | Biere-Citron et al. .... | 424/142.1 |
| 2003/0082547 A1 * | 5/2003 | Ewing .................. | C07C 245/08 435/6.12 |

(Continued)

FOREIGN PATENT DOCUMENTS

| | | |
|---|---|---|
| AU | 199349497 B2 | 3/1994 |
| AU | 199898131 B2 | 3/1999 |

(Continued)

OTHER PUBLICATIONS

U.S. Appl. No. 12/606,818, filed Oct. 27, 2009.
U.S. Appl. No. 12/563,330, filed Sep. 21, 2009.
WO, International Search Report and Written Opinion PCT/US09/62382, 8 pages, dated Mar. 31, 2010.
WO, International Search Report and Written Opinion PCT/US2009/057681, 13 pages, dated Feb. 3, 2010.
Abulrob et al., "The blood-brain barrier transmigrating single domain antibody: mechanisms of transport and antigenic epitopes in human brain endothelial cells," Journal of Neurochemistry, 2005, 95:1201-1214.

(Continued)

*Primary Examiner* — Chang-Yu Wang
(74) *Attorney, Agent, or Firm* — Kagan Binder, PLLC.

(57) ABSTRACT

Blood-brain barrier permeable peptide compositions that contain variable antigen binding domains from camelid and/or shark heavy-chain only single-domain antibodies are described. The variable antigen binding domains of the peptide compositions bind to therapeutic and diagnostic biomarkers in the central nervous system, such as the amyloid-beta peptide biomarker for Alzheimer's disease. The peptide compositions contain constant domains from human IgG, camelid IgG, and/or shark IgNAR. The peptide compositions include heavy-chain only single-domain antibodies and compositions with one or more variable antigen binding domain bound to one or more constant domains.

10 Claims, 9 Drawing Sheets

Specification includes a Sequence Listing.

(56) References Cited

U.S. PATENT DOCUMENTS

| | | |
|---|---|---|
| 2004/0137570 A1 | 7/2004 | Grosveld |
| 2005/0009050 A1 | 1/2005 | Nadeau et al. |
| 2005/0037421 A1 | 2/2005 | Honda et al. |
| 2005/0136493 A1 | 6/2005 | Rubin et al. |
| 2005/0152896 A1 | 7/2005 | Aaron et al. |
| 2006/0246477 A1 | 11/2006 | Hermans et al. |
| 2007/0117151 A1 | 5/2007 | Frederix et al. |
| 2007/0160616 A1 | 7/2007 | Rosenthal et al. |
| 2007/0248604 A1 | 10/2007 | Desnoyers et al. |
| 2008/0057054 A1 | 3/2008 | Annaert et al. |
| 2008/0107601 A1* | 5/2008 | Lauwereys et al. ............ 424/9.1 |
| 2009/0148438 A1* | 6/2009 | Nuttal .................. C07K 14/461 424/133.1 |
| 2009/0162358 A1* | 6/2009 | Alard et al. ............... 424/136.1 |
| 2009/0230322 A1* | 9/2009 | Russell ............ G01N 33/54346 250/459.1 |
| 2010/0092470 A1* | 4/2010 | Bhatt et al. ................ 424/133.1 |
| 2010/0136584 A1* | 6/2010 | Bhatt et al. ................... 435/7.23 |
| 2010/0143353 A1* | 6/2010 | Mosser et al. ............. 424/133.1 |
| 2010/0266686 A1* | 10/2010 | Horn et al. .................... 424/477 |
| 2011/0014182 A1* | 1/2011 | Alard et al. ............... 424/130.1 |
| 2011/0135662 A1* | 6/2011 | Finney et al. ............. 424/172.1 |
| 2011/0275857 A1* | 11/2011 | Lawson ........................ 564/123 |
| 2012/0003214 A1* | 1/2012 | Nuttall ................. C07K 14/461 424/133.1 |
| 2012/0059155 A1* | 3/2012 | Evans et al. ............... 530/387.3 |
| 2012/0164068 A1* | 6/2012 | Hudson et al. .............. 424/1.49 |
| 2012/0259096 A1* | 10/2012 | Miller et al. ............... 530/387.9 |
| 2012/0263727 A1* | 10/2012 | Baker ........................ 424/139.1 |
| 2012/0263728 A1* | 10/2012 | Baker ........................ 424/139.1 |
| 2013/0310281 A1* | 11/2013 | Harding ................. C07K 16/22 506/18 |
| 2016/0237169 A1* | 8/2016 | Nuttall ................. C07K 14/461 |

FOREIGN PATENT DOCUMENTS

| | | | |
|---|---|---|---|
| EP | 1 024 191 A2 | 8/2000 | |
| EP | 1 264 885 A1 | 12/2002 | |
| EP | 1 978 035 A1 | 10/2008 | |
| WO | WO 1994/025591 A1 | 11/1994 | |
| WO | WO 1999/042077 A2 | 8/1999 | |
| WO | WO 2000/043507 A1 | 7/2000 | |
| WO | WO 2001/090190 A2 | 11/2001 | |
| WO | WO 2002/048193 A2 | 6/2002 | |
| WO | WO 2002/057445 A1 | 7/2002 | |
| WO | WO 2004/044204 A | 5/2004 | |
| WO | WO2004/081026 * | 9/2004 | |
| WO | WO 2006/054991 A1 | 5/2006 | |
| WO | WO 2007/035092 A2 | 3/2007 | |
| WO | WO 2009/135853 A2 | 11/2009 | |
| WO | WO2010/033913 * | 3/2010 | ............. C12P 21/08 |
| WO | WO 2010/033913 A1 | 3/2010 | |
| WO | WO 2010053788 A1 | 5/2010 | |

OTHER PUBLICATIONS

Ahmadvand et al., "High-Expression of Monoclonal Nanobodies used in the Preparation of HRP-Conjugated Second Antibody," Hybridoma, 2008, 27(4):269-276.

Ahmadvand et al., "Production and Characterization of a High-Affinity Nanobody Against Human Endoglin," Hybridoma, 2008, 27(5):353-360.

Alvarez-Rueda et al., "Generation of llama single-domain antibodies against mathottrexate, a prototypical hapten," Molecular Immunology, 2007, 44:1680-1690.

Anderson et al., "TNT detection using llama antibodies and a two-step competitive fluid array immonoassay," Journal of Immunological Methods, 2008, 339;47-54.

Azwai et al., "The Isolation and Characterization of Camel (*Camelus dromedarius*) Immunoglobalin Classes and Subclasses," J. Gomp. Path., 1993, 109:187-195.

Behar et al., "Llama single-domain antibodies directed against nonconventional epitopes of tumor-associated carcinoembryonic antigen absent from nonspecific cross-reacting antigen," FEBS Journal, 2009, 276:3881-3893.

Blier et al., "A Limited Number of B Cell Lineages Generates the Heterogeneity of a Secondary Immune Response," Journal of Immunology, Dec. 15, 1987, 139(12):3996-4006.

Boado et al, "GDNF Fusion Protein for Targeted-Drag Delivery Across the Human Blood-Brain Barrier," Wiley Periodicals, Inc., Biotechnology and Bioengineering, 2007, 100(2):387-396.

Chen et al., "Construction of a Large Phage-Displayed Homan Antibody Domain Library with a Scuffold Based on a Newly Identified Highly Soluble, Stable Heavy Chain Variable Domain," J. Mol. Biol., 2008, 382:779-789.

Coloma et al., "Transport Across the Primate Blood-Brain Barrier of Genetically Engineered Chimeric Monoclonal Antibody to the Human Insulin Receptor," Pharmaceutical Research, 2000, 17(3):266-274.

Conrath et al., "Antigen Binding and Solubility Effects upon the Veneering of a Camel VHH in Framework-2 to Mimic a VH," J. Mol. Biol., 2005, 350:112-125.

Conrath et al., "Camel Single-domain Antibodies as Modular Building Units in Bispecific and Bivalent Antibody Constructs," Journal of Biological Chemistry, Mar. 9, 2001, 276(10):7346-7350.

Conrath et al., "Emergence and evolution of functional heavy-chain antibodies in *Camelidae*," Developmental and Comparative Immunology, 2003, 27:87-103.

Conrath et al., "β-Lactamase Inhibitors Derived from Single-Domain Antibody Fragments Elicited in the *Camelidae*," Antimicrobial Agents and Chemotherapy, Oct. 2001, 45(10):2807-2512.

Coppieters et al., "Formatted Anti-Timor Necrosis Factor a VHH Proteins Derived from Camelids Show Superior Potency and Targeting to Inflamed Joints in a Murine Model of Collagen-Induced Arthritis," Arthritis & Rheumatism, Jun. 2006, 54(6): 1856-1866.

Cortez-Retamozo et al., "Efficient Tumor Targeting by Single Domain Antibody Fragments of Camels," Int. J. Cancer, 2002, 98:456-462.

Daley at al, "Application of Monoclonal Antibodies in Functional and Comparative Investigations of Heavy-Chain immunoglobulins in New World Camelids," Clinical and Diagnostic Laboratory Immunology, Mar. 2005, 12(3):380-386.

De Genst et al., "Antibody repertoire development in camelids," Developmental and Comparative Immunology, 2006, 30:187-198.

De Genst et al.,"Chemical Basis for the Affinity Maturation of a Camel Single Domain Antibody," Journal of Biological Chemistry, Dec. 17, 2004, 279(51):53593-53601.

De Genst et al., "Molecular basis for the preferential cleft recognition by dromedary heavy-chain antibodies," PNAS, Mar. 21, 2006, 103(12):4586-4591.

De Haard et al., "Llama Antibodies against a Lactococcal Protein Located at the Tip of the Phage Tail Prevent Phage Infection," Journal of Bacteriology, Jul. 2005, 187(13):4531-4541.

Decanniere et al., "Degenerate interfaces in Antigen-Antibody Complexes," J. Mol. Biol., 2001, 313:473-478.

Deckers et al., "Nanobodies, a promising tool for species-specific diagnosis of *Taenla solium* cysticercosis," International Journal for Parasitology, 2009, 39:625-633.

Deffar et al, "Nanehodies—the new concept in antibody engineering," African Journal of Biotechnology, Jun. 17, 2009, 8(12):2645-2652.

Desmyter et al., "Antigen Specificity and High Affinity Binding Provided by One Single Loop of a Camel Single-domain Antibody," J. Biol. Chem., Jul. 13, 2001, 276(28):26285-26290.

Desmyter et al., "Crystal structure of a camel single-domain VH antibody fragment in complex with lysozyme," Nature Publishing Group, Nature Structural Biology, 1996, 3(9):803-811.

Dooley et al., "Shark immunity bites back: affinity muturation and memory response in the nurse shark, *Ginglymostoma cirratum*," WILEY-VCH GambH & Co. KGaA, European Journal Immunology, 2005, 35:936-945.

Doyle et al., "Intracellular Expression of a Single Domain Antibody Reduces Cytotoxicity of 15-Acelyldeoxynivalenol in Yeast," J. Biol. Chem., Dec. 11, 2009, 284(50):35029-35039.

(56) References Cited

OTHER PUBLICATIONS

Dumoulin et al., "Single-domain antibody fragments with high conformational stability," Protein Science, Mar. 2002, 11(3):500-515.
Edelman et al., "The Antibody Problem," Annual Reviews Biochemistry, 1969, 38:415-466.
Egleton et al., "Development of Neuropeptide Drugs that Cross the Blood-Brain Barrier," The Journal of the American Society for Experimental NeuroTherapeutics, Jan. 2005, 2:44-53.
El Khattabi et al,. "Llama Single-Chain Antibody that Blocks Lipopolysaccharide Binding and Signaling: Prospects for Therapeutic Applications," Clinical and Vaccine Immunology, Oct. 2006, 33(10):1079-1086.
Ewert et al., "Biophysical Properties of Camelid VHH Domains Compared to Those of Human $V_H3$ Domains," Biochemistry, 2002, 41:3628-3636.
Ferrari et al., "Immunobiological role of llama heavy-chain antibodies against a bacterial β-lactamase," Veterinary Immunology and Immunopathology, 2007, 117:173-182.
Forsman et al., "Llama Antibody Fragments with Cross-Subtype Human Immunodeficiency Virus Type 1 (HIV-1)-Neutralizing Properties and High Affinity for HIV-1 gp120," Journal of Virology, Dec. 2008, 82(24):12069-12081.
Frenken et al., "Isolation of antigen specific Llama VHH antibody fragments and their high level secretion by *Saccharomyces cerevisiae*," Journal of Biotechnology, 2000, 78:11-21.
Ghahroudi et al., "Selection and identification of single domain antibody fragments from camel heavy-chain antibodies," FEBS Letters, 1997, 414:521-526.
Goldman et al., "Facile Generation of Heat Stable Antiviral arid Antitoxin Single Domain Antibodies from a Semi-synthetic Llama Library," Anal. Chem., Dec. 15, 2006, 78(24):8245-8255.
Goldman et al., "Thermostable Llama Single Domain Antibodies for Detection of Botulinum A Neurotoxin Complex," Anal. Chem., 2008, 80:8583-8591.
Gottlin et al., "Isolation of Novel EGFR-Specific VHH Domains," Journal of Biomolecular Screening, 2009, 14(1):77-85.
Greenberg et al., "A new antigen receptor gene family that undergoes rearrangement and extensive somatic diversification in sharks," Nature, Mar. 9, 1995, 374:168-173.
Grover et al., "Preliminary Studies on Camel Serum Immunoglobilins," Indian Journal of Biochemistry & Biophysics, 1983, 20:238-240.
Habicht et al., "Directed selection of a conformational antibody domain that prevents mature amyloid fibril formation by stabilizing AP protofibrils," PNAS, Dec. 4, 2007, 104(49):19232-19237.
Hamers-Casterman et al., "Naturally occurring antibodies devoid of light chains," Nature, Jun. 3, 1993, 363:446-448.
Harmsen et al., "Properties, production and applications of camelid single-domain antibody fragments," Appl. Microbiol. Biotechnol., Nov. 2007, 77(1):13-22.
Harmsen et al., "Selection and optimization of proteolyticaliy stable llama single-domain antibody fragments for oral immunotherapy," Appl. Microbiol. Biotechnol., 2006, 72:544-551.
Harrison et al., "Neutralisation of venom-induced haemorrhage by IgG from camels and llamas immunized with viper venom and also by endogenous, non-IgG components in camelid sera," Toxicon, 2006, 47:364-368.
Hmila et al., "VHH, bivalent domains and chimeric Heavy chain-only antibodies with high neutralizing efficacy for scorpion toxin Aahl'," Molecular Immunology, 2008, 45;3847-3856.
Holliger et al., "Engineered antibody fragments and the rise of single domains," Nat. Biotechnol., Sep. 2005, 23(9):1126-1136.
Holt et al., "Domain antibodies: proteins for therapy," Trends in Biotechnology, Nov. 2003, 21(11):484-490.
Huang et al, "Prostate-specific antigen immunosensing based on mixed self-assembled monolayers, camel antibodies and colloidal gold enhanced sandwich assays," Biosensors and Bioelectronics, 2005, 21:483-490.

Jespers et al., "Crystal Structure of HEL4, a Soluble, Refoldable Human $V_H$ Single Domain with a Germ-line Scaffold," J. Mol. Biol., 2004, 337:893-903.
Jobling et al., "Immunomodulation of enzyme function in plants by single-domain antibody fragments," Nature Biotechnology, 2003, 21:77-80.
Kastelic et al., "A single-step procedure of recombinant library construction for die selection of efficiently produced llama VH binders directed against cancer markers," Journal of Immunological Methods, 2009, 350:54-62.
Klooster et al., "Improved anti-IgG and HAS affinity ligands: Clinical application of VHH antibody technology," Journal of Immunological Methods, 2007, 324:1-12.
Koch-Nolte et al., "Single domain antibodies from llama effectively and specifically block T cell ecto-ADP-ribosyltransferase ART2.2 in vivo," The FASEB Journal, Nov. 2007, 21:3490-3498.
Lafaye et al., "Single-domain antibodies recognize selectively small oligomeric forms of amyloid 13, prevent AP-induced neurotoxicity and inhibit fibril formation," Molecular Immunology, 2009, 46:695704.
Lauwereys et al., "Potent enzyme inhibitors derived from dromedary heave-chain antibodies," The EMBO Journal, 1998, 17(13):3512-3520.
Lewis et al., "Construction and Evaluation of Novel Fusion Proteins for Targeted Delivery of Micro Particles to Cellulose Surfaces," Biotechnology and Bioengineering, Jul. 5, 2006, 94(4):625-632.
Li et al., "Pentabody-mediated antigen delivery induces antigen-specific mucosal immune response," Molecular Immunology, 2009, 46:1718-1726.
Liu et al., "Selection of cholera toxin specific IgNAR single-domain antibodies form a naive shark library," Molecular Immunology, 2007, 44:1775-1783.
Maass et al., "Alpaca (*Lama pacos*) as a convenient source of recombinant camelid heave chain antibodies (VHHs)," Journal of Immunological Methods, 2007, 324:13-25.
Malecek et al., "Immunoglobulin Heavy Chain Exclusion in the Shark," PLOS Biology, Jun. 2008, 6(6):1226-1242.
Marquardt et al., "A Synthetic Camel Anti-Lysazyme Peptide Antibody (Peptibody) with Flexible Loop Structure Identified by High-Resolution Affinity Mass Spectrometry," Chem. Eur. J., 2006, 12:1915-1923.
Meli et al., "Direct in Vivo Intracellular Selection of Conformation-sensitive Antibody Domains Targeting Alzheimer's Amyloid-β Oligomers," J. Mol. Biol., 2009, 387:584-606.
Monegal et al., "Immunological applications of single-domain llama recombinant antibodies isolated from a naive library," Protein Engineering, Design & Selection, 2009, 22(4):273-280.
Muruganandam et al., "Selection of phage-displayed llama single-domain antibodies that transmigrate across human blood-brain barrier endothelium," The FASEB Journal, express article 10.1096/fj/01-0343fje, published online Dec. 28, 2001, 22 pages.
Muyldermans et al., "Camelid immunoglobulins and nanobody technology," Veterinary Immunology and Immunopathology, Mar. 15, 2009, 128(1-3):178-183.
Muyldermans et al., "Recognition of antigens by single-domain antibody fragments: the superfluous luxury of paired domains," Trends in Biochemical Sciences, Apr. 2001, 26(4):230-235.
Muyldermans et al., "Sequence and structure of VH domain from naturally occurring camel heavy chain immunoglobulins lacking light chains," Protein Engineering, 1994, 7(9)1129-1135.
Muyldermans et al., "Unique single-domain antigen binding fragments derived from naturally occuring camel heavy-chain antibodies," Journal of Molecular Recognition, 1999, 12:131-140.
Muyldermans, Serge, "Single domain camel antibodies: current status," Reviews in MolecularBiotech., Jun. 2001, 74(4):277-302.
Nguyen et al., "Camel heavy-chain antibodies: diverse germline $V_HH$ and specific mechanisms enlarge the antigen-binding repertoire," The EMBO Journal, 2000, 19(5):921-930.
Nguyen et al., "Heavy-chain antibodies in *Camelidae*; a case of evolutionary innovation," Immunogenetics, 2002, 54:39-47.
Nguyen et al., "Heavy-chain only antibodies derived from dromedary are secreted and displayed by mouse B cells," Immunology, 2003, 109:93-101.

(56) References Cited

OTHER PUBLICATIONS

Nguyen et al., "The Specific Variable Domain of Camel Heavy-chain Antibodies is Encoded in the Germline," J. Mol. Biol., 1998, 275:413-418.
Nuttall et al., "Isolation of the new antigen receptor from wobbegong sharks, and use of a scaffold for the display of protein loop libraries," Molecular Immunology, 2001, 38:313-326.
Nuttall et al., "Selection and Affinity Maturation of IgNAR Variable Domains Targeting *Plasmodium falciparum* AMA1," Proteins: Structure, Function, and Bioinformatics, 2004, 55:187-197.
Omidfar et al., "Expression of EGFRvIII in Thyroid Carcinoma: Immunohistochemical Study by Camel Antibodies," Immunological Investigations, 2009, 38:165-180.
Omidfar et al,, "Production and Characterization of a New Antibody Specific for the Mutant EGF Receptor, EGFRvIII, in *Camelus bactrianus*," Tumor Biol., 2004, 25:179-187.
Omidfar et al., "Production of a Novel Caind Single-Domain Antibody Specific for the Type III Mutant EGFR," Tumor Biol., 2004, 25:296-305.
Perruchini et al., "Llama VHH antibody fragments against GFAP: better diffusion in fixed tissues than classical monoclonal antibodies," Acta Neuropathol., 2009, 118:685-695.
Pleschberger et al., "Generation of a Functional Monomolecular Protein Lattice Consisting of an S-Layer Fusion Protein Comprising the Variable Domain of a Camel Heavy Chain Antibody," Bioconjugate Chem., 2003, 14:440-448.
Rahbarizadeh et al., "High expression and purification of the recombinant camelid anti-MUC1 single domain antibodies in *Escherichia coli*," Protein Expression and Purification, 2005, 44:32-38.
Rahbarizadeh et al., "Over expression of anti-MUC1 single-domain antibody fragments in the yeast *Pichia pastoris*," Molecular Immunology, 2006, 43:426-435.
Rahbarizadeh et al., "Production of Novel Recombinant Single-Domain Antibodies against Tandem Repeat Region of MUC1 Mucin," Hybridoma and Hybridomics, Nov. 3, 2004, 23:151-159.
Renisio et al., "Solution Structure and Backbone Dynamics of an Antigen-Free Heavy Chain Variable Domain (VHH) From *Llama*," Proteins: Structure, Function and Genetics, 2002, 47:546-555.
Riechmann et al., "Single domain antibodies: comparison of camel VH and camelised human VH domains," J. Immunol. Methods, Dec. 10, 1999, 231(1-2):25-38.
Rothbauer el al., "Targeting and tracing antigens in live cells with fluorescent nanobodies," Nature Methods, Nov. 2006, 3(11):887-889.
Roux et al., "Structural analysis of the nurse shark (new) antigen receptor (NAR): Molecular convergence of NAR and unusual mammalian immunoglobulins," Proc. Natl. Acad. Sci. USA, Sep. 1998, 95:11804-11809.
Saerens et al., "Antibody Fragments as Probe in Biosensor Development," Sensors, 2008, 8:4669-4686.
Saerens et al., "Engineering Camel Single-Domain Antibodies and Immobilization Chemistry for Human Prostate-Specific Antigen Sensing," Anal. Chem., 2005, 77:7547-7555.
Saerens et al., "Identification of a Universal VHH Framework to Graft Non-canonical Antigen-binding Loops of Camel Single-domain Antibodies," J. Mol., Biol., 2005, 352:597-607.
Saerens el al., "Parallel selection of multiple anti-infectome Nanobodies without access to purified antigens," Journal of Immunological Methods, 2008, 329:138-150.
Saerens et al,, "Single Domain Antibodies Derived from Dromedary Lymph Node and Peripheral Blood Lymphocytes Sensing Conformational Variants of Prostate-specific Antigen," J. Biol. Chem., Dec. 10, 2004, 279(50):51965-51972.
Saerens et al., "Single-domain antibodies as building blocks for novel therapeutics," Current Opinion in Pharmacology, 2008, 8:600-608.
Sehrawat et al., "Anti-crythrocyte natural antibody activity in the unconventional 'heavy chain' immunoglobulins of Indian desert camel (*Camelus dromedarius*),"Veterinary Immunology and Immunopathology, 2006, 111:139-147.
Shao et al., "Rapid isolation of IgNAR variable single-domain antibody fragments from a shark synthetic library," Molecular Immunology, Jan. 2007, 44(4):656-665.
Sonneson et al., "Hapten-Induced Dimerization of a Single-Domain VHH Camelid Antibody," Biochemistry, 2009, 48:6693-6695.
Spinelli et al., "Camelid Heavy-Chain Variable Domains Provide Efficient Combining Sites to Haptens," Biochemistry, 2000, 39:1217-1222.
Stanfield et al., "Crystal Structure of a Shark Single-Domain Antibody V Region in Complex with Lysozyme," Science, Sep. 17, 2004, 305:1770-1773.
Streltsov et al., "Crystal Structures of Shark Immunoglobulin New Antigen Receptors (IgNARs)," Photon Factory Activity Report 2004, #22 Part B (2005), 2005, 216.
Streltsov et al., "Structure of a shark IgNAR antibody variable domain and modeling of an early-developmental isotype," Protein Science, 2005, 14:2901-2909.
Transue et al., "Camel Single-Domain Antibody Inhibits Enzyme by Mimicking Carbohydrate Substrate," Proteins: Structure, Function and Genetics, 1998, 32:515-522.
Ungar-Waron et al., "Dromedary IgG: Purification, characterization and quantitation in sera of dams and newborns," 'sr. J. Vet. Med., 1987, 43(3):198-203.
Van Der Linden et al., "Comparison of physical chemical properties of llama VHH antibody fragments and mouse monoclonal antibodies," Biochimica et Biophysica Acta, 1999, 1431:37-46.
Van Der Linden et al., "Induction of immune responses and molecular cloning of the heavy chain antibody repertoire of *Lama glama*," Journal of Immunological Methods, 2000, 240:185-195.
Van Der Vaart et al., "Reduction in morbidity of rotnvirus induced diarrhoea in mice by yeast produced monovalent llama-derived antibody fragments," Vaccine, May 8, 2006, 24(19):4130-4137.
Veiga et al., "Structural tolerance of bacterial autotransporters for folded passenger protein domains," Molecular Microbiology, 2004, 52(4):1069-1080.
Verheesen et al., "Beneficial properties of single-domain antibody fragments for application in immunoaffinity purification and immunoperfusion chromatography," Biochimica et Biophysica Acta, 2003, 1624:21-28.
Vincke et al., "Camel antibodies for therapeutic and research applications," Proceedings of International Camel Conference, Bikaner, Feb. 16-17, 2007, 71-75.
Vincke et al., "General Strategy to Humanize a Camelid Single-domain Antibody and Identification of a Universal Humanized Nanobody Scaffold," The Journal of Biological Chemistry, Jan. 30, 2009, 284(5)3273-3284.
Ward et al., "Binding activities of a repertoire of single immunoglobulin variable domains secreted from *Escherichia coli*," Nature, Oct. 12, 1989, 341:544-546.
Wesolowski et al., "Single domain antibodies: promising experimental and therapeutic tools in infection and immunity," Med. Microbiol. Immunol., 2009, 198:157-174.
Zarebski et al., "Llama Single Domain Antibodies as a Tool for Molecular Mimicry," J. Mol. Biol., 2005, 349:814-824.
R.M. Koffie, et al., "Nanoparticles enhance brain delivery of blood-brain barrier-impermeable probes for in vivo optical and magnetic resonance imaging", *Proc. of Nat. Acad. Sci.*, vol. 108, No. 46, pp. 18837-18842, PX055110283 (Nov. 2011).
Rob J.A. Nabuurs, et al., "In Vivo Detection of Amyloid-[beta] Deposits Using Heavy chain Antibody Fragments in a Transgenic Mouse Model for Alzheimer's Disease", *Plos One*, vol. 7, No. 6, p. e38284, XP055097899 (Jun. 2012).
EP, Extended European Search Report, Application No. 13171872.8, dated Feb. 3, 2016.

* cited by examiner

Naturally occurring single-domain
Antibody 1 (sd-Ab) : R = H
(Molecular Weight: ~90KDa)

BBB Permeable Proposed sd-Ab Analog 2:
(Molecular Weight: ~ 50-55 KDa)

FIG. 7
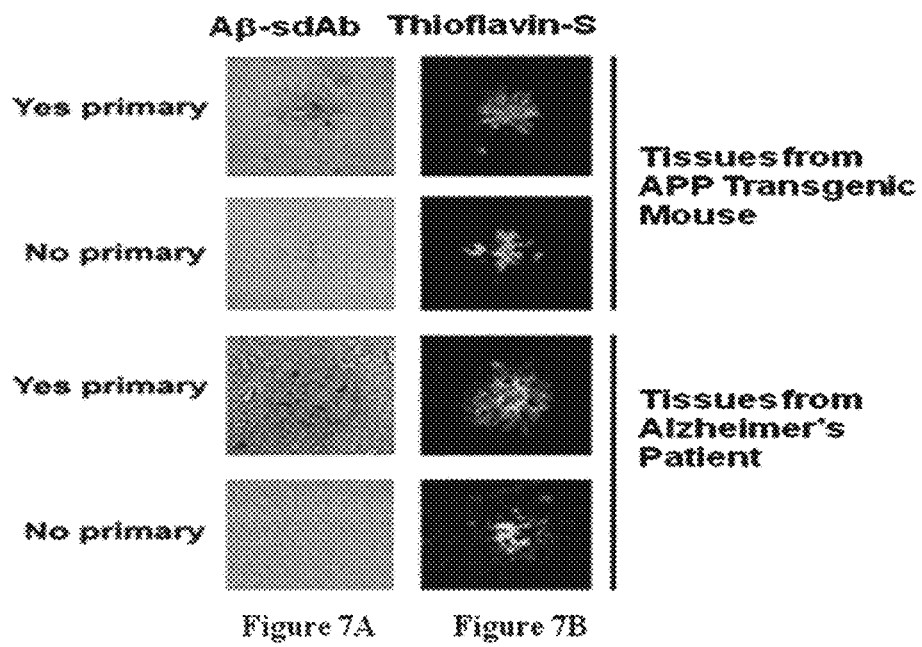
Figure 7A     Figure 7B
FIG. 8
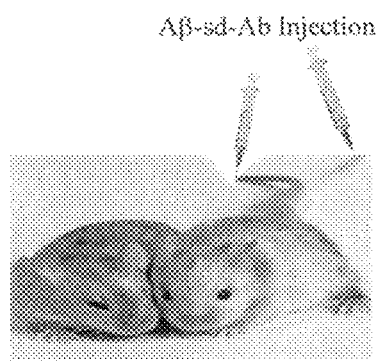

METHODS OF ASSESSING AMYLOID-BETA PEPTIDES IN THE CENTRAL NERVOUS SYSTEM BY BLOOD-BRAIN BARRIER PERMEABLE PEPTIDE COMPOSITIONS COMPRISING A VAB DOMAIN OF A CAMELID SINGLE DOMAIN HEAVY CHAIN ANTIBODY AGAINST AN ANTI-AMYLOID-BETA PEPTIDE

CROSS REFERENCE TO RELATED PATENT APPLICATIONS

This application is a continuation in part of U.S. application Ser. No. 13/736,852, filed Jan. 8, 2013, and claims the benefit under 35 U.S.C. 0119(e) of the U.S. Provisional Application 61/631,731, filed Jan. 9, 2012, the contents of each of which is hereby incorporated by reference in its entirety into the present disclosure.

SEQUENCE LISTING

The instant application contains a Sequence Listing which has been submitted in ASCII format via EFS-Web and is hereby incorporated by reference in its entirety. Said ASCII copy, created on Feb. 12, 2013, is named 095299-0110_SL.txt and is 8,591 bytes in size.

FIELD OF THE INVENTION

The invention relates to the discovery of blood-brain barrier (BBB) permeable peptide compositions and antibody-mimics derived from camelid and shark heavy-chain only antibodies, their analogs, and uses thereof.

BACKGROUND OF THE INVENTION

A. The Blood-Brain Barrier

The blood-brain barrier (BBB) has been an impediment to successful drug delivery to the central nervous system (CNS). As a consequence, most diseases of the brain cannot be diagnosed and treated. Typically, only small-molecule drugs cross the BBB. That is why, for too long, the process of drug discovery has been centered on designing, developing and screening small molecules with activity at a particular site or receptor in the brain. However, small-molecule drugs for CNS targets have limitations, which include: i) non-specific targeting; ii) non-specific organ distribution; iii) low therapeutic indices; iv) development of drug resistance shortly after initial treatment; v) only a small percentage of small-molecule drugs cross the BBB and vi) only 1% of the total number of drugs were active in the CNS [Partridge W M, NeuroRX, 2 (1), 3 (2006)]. In addition, only a few diseases of the brain, such as depression, chronic pain, and epilepsy, respond to this category of small molecules. Most serious diseases of the brain such as Alzheimer's disease (AD); Parkinson's disease (PD); brain cancer; stroke; brain and spinal cord injury; HIV infection of the brain; Huntington disease; multiple sclerosis (MS); and many childhood inborn genetic errors affecting the brain do not respond to small molecule drugs, irrespective of the lipid solubility of the drug. A handful of FDA approved small molecule drugs, e.g. Aricept (AD), Cognex (AD), Exelon (AD), Razadyne (AD), and Levodopa (PD), for neurodegenerative diseases that slow down the disease symptoms in some patients stop working after a period of time, leaving the patient to helplessly succumb to his/her disease.

Development of large molecule drugs is generally discouraged because of their typically poor BBB permeability. Many potential large molecule modern drugs, such as, engineered proteins (e.g.: nerve growth factors), antibodies, genes, vectors, micro-RNA, siRNA, oligonucleotides and ribozymes, which are otherwise effective in ex-vivo studies, have not been developed for clinical use due to a failure to deliver them in sufficient quantity into the CNS. Although Alzheimer's disease (AD) has been known for more than a century and despite enormous research efforts both by private sectors and government institutes, there are no diagnostics or curative treatments for diseases of the CNS. More than 55 million people (and 6.5 million Americans in the US are afflicted worldwide by neurodegenerative diseases (Alzheimer's disease and Parkinson's disease are the most common forms of degenerative dementia). These troubling statistics demonstrate an unmet need of developing technologies to solve the issues of diagnosing and treating neurodegenerative and tumor diseases in the CNS.

The BBB is formed by light junctions between the cerebral endothelial cells, which are produced by the interaction of several transmembrane proteins that project into and seal the paracellular pathways (FIG. 1). The interaction of these junctional proteins, particularly, occludin and claudin, is complex and effectively blocks an aqueous route of free diffusion for polar solutes from blood along these potential paracellular pathways and thus denies these solutes free access to cerebrospinal fluid. Major scientific efforts over the years have led to the development of the following methods to cross the BBB: (i) The use of liposomes or other charged lipid formulations, widen base limited complex stability in serum and high toxicity over time (Whittlessey K J et al., Biomaterials, 27, 2477 (2006)); (ii) Electroporation-based techniques which are only effective when performed during a specific window of development in healthy cells, with eventual loss of expression or bioactivity (Gartner et al., Methods Enzymology 406, 374 (2006)), and (iii) Viral-based vectors and fusions which have shown only limited efficacy in humans and animals while raising a number of safety concerns, and typically requiring invasive procedures such as direct injection into the brain to achieve targeted delivery (Luo D, Nat Biotechol, 18 (8), 893 (2000)). Thus, there is an unmet need to develop novel technologies to breach the BBB.

B. Strategies for Drug Delivery Across the Blood-Brain Barrier

Invasive strategies such as intra-cerebroventricular infusion, convection-enhanced delivery, and intracerebral injection are covered in the following references: Pardridge W M, Pharma Res., 24, 1733 (2007); Pardridge W M, Nevro RX 2, 3 (2005); Vandergrift W A, et al., Neurosurg Focus, 20, E10 (2006); Funk L K, et al., Cancer Res., 58, 672 (1998); Marks W J, et al., Lancet Neurol, 7, 400 (2008); and Herzog C D, et al., Mov. Disord, 22, 1124 (2007).

Disruption of the BBB using bradykynin analogues, ultrasound, and osmotic pressure are covered in the following references: Borlogan C V, et al., Brain Research Bulletin, 60, 2970306 (2003); Hynysen K, et al., J. Neurosurg., 105, 445 (2006); and Fortin D, et al., Cancer, 109, 751 (2007).

Physiological approaches involving transporter-mediated delivery, receptor-mediated transcytosis, adsorptive-mediated transcytosis are covered in the following references: Allen D D, et al., J. Pharmacol Exp Ther, 304, 1268 (2003); Coloma M J, et al., Pharm Res, 17, 266 (2000); Jones A R, et al., Pharma Res, 24, 1759 (2007); Boada R J, et al., Biotech Bioeng, 100, 387 (2007); Pardridge W M, Pharma Res, 3, 90 (2003); Zhang Y, et al., *J. Pharmaco Exp Therap*, 313, 1075 (2005); and Zhang Y, et al, *Brain Res*, 1111, 227 (2006).

Pharmacological approaches involving chemical modification of drugs to lipophilic molecules or encapsulation into liposomes are covered by the following references: Bradley M O, Webb N L, et al., *Clin. Cancer Res.*, 7, 3229 (2001); Lipinki C A, Lombardo F, et al., *Adv. Drug Deliv Rev.*, 46, 3 (2001); Huwyler J, et al., *J. Pharmacol Exp Ther*, 282, 1541 (1997); Madrid Y, et al., *Adv Pharmacol*, 22, 299 (1991); Huwyler J, Wu D, et al., *Proc. Natl. Acad. Sci. USA*, 93, 14164 (1996); Swada G A, et al., *J. Pharmacol Exp Ther*, 281, 1327 (1999); and Shashoua V E, et al., *Life Sci.*, 1347 (1996).

Resistance to opsonization and nanoparticles based drug delivery across the BBB, whereby the drug is passively adsorbed on to the particles, is covered by following references: Greiling W, Ehrlich P, Verlag E, Dusseldorf, Germany, p. 48, 1954; Couvreur P, Kante B, et al., *J. Pharm Pharmacol*, 31, 331 (1979); Douglas S J, et al., *J. Colloid. Interface Sci*, 101, 149 (1984); Douglas S J, et al., *J. Colloid Interface Sci.*, 103, 154 (1985); Khanna S C Speiser P, *J. Pharm. Sci*, 58, 1114 (1969); Khanna S C et al., *J. Pharm. Sci*, 59, 614 (1970); Sugibayashi K, et al., *J. Pharm. Dyn*, 2, 350 (1979b); Brasseur F, Couvreur P, et al., Actinomycin D absorbed on polymethylcyanoacrylate: increased efficiency against an experimental tumor, *Eur. J. Cancer*, 16, 1441 (1980); Widder K J, et al., *Eur. J. Cancer*, 19, 141 (1983); Couvreur P, et al., Toxicity of polyalkylcyanoacrylate nanoparticles II. Doxorubicin-loaded nanoparticles, *J. Pharma Sci*, 71, 790 (1982); Couvreur P, et al., Biodegradable polymeric nanoparticles as drug carrier for antitumor agents, *Polymeric Nanoparticles and Microspheres*, CRC Press, Boca Raton, pp. 27-93 (1986); Grislain L, Couvreur P, et al., Pharmacokinetics and distribution of a biodegradable drug-carrier, *Int. J. Pharm.*, 15, 335 (1983); Mukherjee P, et al., Potential therapeutic applications of gold nanoparticles in BCLL, *J. Nanobiotechnology*, 5, 4 (2007); Maeda H and Matsumura Y, Tumoritropic and lymphotropic principles of macromolecular drugs, *Crit. Rev. Ther. Drug Carrier Syst.*, 6, 193 (1989); Kattan, J et al., Phase I clinical trial and pharmacokinetic evaluation of doxorubicin carried by poly-isohexylcyanoacrylate nanoparticles, *Invest. New Drugs*, 10, 191 (1992); Kreuter J, Nanoparticles-A historical perspective, *Int. J. Pharm.*, 331, 1 (2007); Alyautdin R, et al., Analgesic activity of the hexapeptide dalargin adsorbed on the surface of polysorbate 80-coated poly(butyl cyanoacrylate) nanoparticles. *Eur. J. Pharm. Biopharm.*, 41, 44 (1995); Kreuter J, Alyautdin R, et al., Passage of peptides through the blood-brain barrier with colloidal polymer particles (nanoparticles), *Brain Res.*, 674, 171 (1995); Alyautdin R N et al., Delivery of loperamide across the blood-brain barrier with Polysorbate 80-coated polybutylcyanoacrylate nanoparticles, *Pharm. Res.*, 14, 325 (1997); Schroeder U, et al., Body distribution of $^3$H-labeled dalargin bound to polybutylcyanoacrylate, *Life Sci.*, 66, 495 (2000); Alyautdin R N et al., Significant entry of tubocurarine into the brain of rats by absorption to polysorbate 80-coated polybutyl-cyanoacrylate nanoparticles: an in situ brain perfusion study, *J. Microencapsul.*, 15, 67 (1998); Gulyaev A E, Gelperina S E, et al., Significant transport of doxorubicin into the brain with polysorbate 80-coated nanoparticles, *Pharm. Res.*, 16, 1564 (1999); Steiniger S C J, Kreuter J. et al., Chemotherapy of glioblastoma in rats using doxorabicin-loaded nanoparticles, *Int. J. Cancer*, 109, 759 (2004); Hekmatara T, et al., Efficient systemic therapy of rat glioblastoma by nanoparticle-bound doxorubicin is due to antiangiogenic effects, *Clin. Neuropath.*, 28, 153 (2009); Gelperina S E, et al., Toxicological studies of doxorubicin bound to polysorbate 80-coated polybutylcyanoacrylate nanoparticles in healthy rats and rats with intracranial glioblastoma, *Toxicol. Lett.*, 126, 131 (2002); Couvreur P, et al., *J. Pharm. Sci*, 71, 790 (1982); Kreuter J, et al., Apolipoprotein-mediated transport of nanoparticles-bound drugs across the blood-brain barrier, *J. Drug Targeting*, 10, 317 (2002); Davis S S, Biomedical applications of nanotechnology-implications for drug targeting and gene therapy, *Tibtech*, 15, 217 (1997); Moghimi S M, Szebeni J, Stealth liposome and long circulating nanoparticles: Critical issues in pharmacokinetics, opsonization and protein-binding properties, *Progress in Lipid Research*, 42, 463 (2003); Arvizo R R, et al., Modulating pharmacokinetics, tumor uptake and biodistribution by engineered nanoparticles, *PLos One*, 6, e24374 (2011); Kurakhmaeva K B, et al., Brain targeting of nerve growth factor using polybutylcyanoacrylate nanoparticles, *J. Drug Targeting*, 17, 564 (2009); and Reukov V, et al., Proteins conjugated to polybutylcyanoacrylate nanoparticles as potential neuroprotective agents, *Biotechnology and Bioengineering*, 108, 243 (2010).

Shortcomings of Nanoparticles. Although nanoparticles have made significant contributions to the field of medical sciences, most of the published studies have been conducted with drugs non-covalently coated to nanoparticles, thereby perhaps not realizing the full potential of nanomedicine.

C. Single-Domain Antibodies

In 1983 it was reported that the sera of camelid contained two different kinds of Immunoglobulin: conventional heterodimeric IgGs composed of heavy and light chains, and unconventional IgGs without the light chains [Grover Y P, et al., *Indian Journal of Biochemistry and Biophysics*, 20, 238 (1983)]. Grover et al. demonstrated the presence of three bands which were designated as IgM, IgA, and a broad heterogeneous band containing a mixture of IgG complexes. One can speculate that the broad band these authors observed was due to the presence of mixture of normal IgG with a molecular weight (MW) of ~160 KDa and heavy-chain IgG, without the light chain, with a MW of ~80 KDa. However, since these authors did not use a proper sizing marker, the broad IgGs band could not be satisfactorily characterized.

Ungar-Waron et al. disclosed a SDS-PAGE analysis of earned IgGs mixture treated with and without 2-mercaptoethanol (2ME) [*Israel J. Vet. Medicine*, 43 (3), 198 (1987)]. In the absence of 2-ME, IgG-complex, obtained from camelid serum, dissociated into two components with approximate molecular weight (MW) of 160 KDa (Conventional IgG) and ~100 KDa (New IgG) on SDS-PAGE. However, in the presence of 2-MEt three bands of MW 55 KDa (gamma-like heavy-Chain), 22 KDa (Light chain) and an additional protein, band of 42 KDa (now known as heavy-chain only camelid antibody band without the light chains) were seen.

Subsequently Azwai et al. from University of Liverpool, UK, independently confirmed the presence of an additional IgG band in camelid seram's with a molecular weight of 42 KDa by SDS-PAGE electrophoresis under reducing conditions [Azwai, S. M., et al., *J. Comp. Path.* 109, 187 (1993)].

Hamers-Casterman et al. also reported similar findings, confirming independently the presence of 42 KDa IgG subclass in the sera of camelids upon SDS-PAGE analysis under reducing conditions [Hamers-Casterman et al., *Nature*, 363, 446 (1993) and U.S. Pat. No. 6,005,079].

Thus, two types of antibodies exist in camels, dromedaries, and llamas; one a conventional hetero-tetramer having two heavy and two light chains (MW~160 KDa), and the other consisting of only two heavy chains, devoid of light chains (MW~80 to 90 KDa).

In addition to camelid antibodies having only two heavy chains and devoid of light chains, a distinctly unconventional antibody isotype was identified in the serum of nurse sharks (Ginglymostoma cirratum) and wobbegong sharks (Orectolobus maculatus). The antibody was called the Ig new antigen receptors (IgNARs). They are disulfide-bonded homodimers consisting of five constant domains (CNAR) and one variable domain (VNAR). There is no light chain, and the individual variable domains are independent in solution and do not appear to associate across a hydrophobic interface [Greenherg A S, Avila D, Hughes M, Hughes A, McKinney E, Flajnik M F, Nature 374, 168 (1995); Nuttall S D, Krishnan U V, Hadarki M, De Gri R, Irving R A, Hudson P J, Mol. Immunol. 38, 313 (2001), Comp. Biochem. Physiol. B., 15, 225 (1973)]. There are three different types of IgNARs characterized by their time of appearance in shark development, and by their disulfide bond pattern [Diaz M, Stanfield R L, Greenberg A S, Flajnik, M F, Immunogenetics, 54, 501 (2002); Nuttall S D, Krishnan U V, Doughty L, Pearson K, Ryan M T, Hoogenraad N J, Hattarki M, Carmichael J A, Irving R A, Hudson P J, Eur. J. Biochem. 270, 3543 (2003)].

The natural hetero-tetrameric structure of antibodies exists in humans and most animals. The heavy-chain only dimer structure is considered natural characteristic of camelids and sharks [Holliger P, Hudson P J, Nature Biotechnology, 23, 1126 (2005)]. These antibodies are relatively simple molecules but with unique characteristics. Since the variable antigen binding (Vab) site binds its antigen only through the heavy-chain, these antibodies are also known as single-domain antibodies (sd-Abs). Their size is about one-half the size of traditional tetrameric antibodies, hence a lower molecular weight (~80 KDa to 90 KDa), with similar antigen binding affinity, hut with water solubility 100- to 1000-fold higher than conventional antibodies.

Another characteristic of heavy-chain antibodies derived from sharks and camelids is that they have very high thermal stability compared to the conventional mAbs. For example, camelid antibodies can maintain their antigen binding ability even at 90° C. [Biochim. Biophys. Acta., 141, 7 (1999)]. Furthermore, complementary determining region 3 (CDR3) of camelid Vab region is longer, comprising 16-21 amino acids than the CDR3 of mouse VH region, comprising 9 amino adds [Protein Engineering, 7, 1129 (1994)]. The larger length of CDR3 of camelid Vab region is responsible for higher diversity of antibody repertoire of camelid antibodies compared to conventional antibodies.

In addition to being devoid of light chains, the camelid heavy-chain antibodies also lack the first domain of the constant region called CH1, though the shark antibodies do have a CH1 domain and two additional constant domains, CH4 and CH5 [Nature Biotech. 23, 1126 (2005)]. Furthermore, the hinge regions (HRs) of camelid and shark antibodies have an amino acid sequence different from that of normal heterotetrameric conventional antibodies [Mulydermans S, Reviews in Mol. Biotech., 74, 277 (2001)]. Without the light chain, these heavy-chain antibodies bind to their antigens by one single domain, the variable antigen-binding domain of the heavy-chain immunoglobulin, which is referred to as Vab in this application (VHH in the literature), to distinguish it from the variable domain VH of the conventional antibodies.

The single-domain Vab is surprisingly stable by itself, without having to be attached to the heavy-chain. This smallest intact and independently functional antigen-binding fragment Vab, with a molecular weight of ~12-15 KDa, derived from a functional heavy-chain only full length. IgG, is referred to as a "nanobody". In the literature [Muyldermans S, Reviews in Mol. Biotech., 74, 277 (2001)].

The genes encoding these full, length single-domain heavy-chain antibodies and the antibody-antigen binding fragment Vab (camelid and shark) can be cloned in phage display vectors, and selection of antigen binders by panning and expression of selected Vab in bacteria offer a very good alternative procedure to produce these antibodies on a large scale. Also, only one domain has to be cloned and expressed to produce in vivo an intact, matured antigen-binding fragment.

There are structural differences between the variable regions of single domain antibodies and conventional antibodies. Conventional antibodies have three constant domains while camelid has two and shark has five constant domains. The largest structural difference is, however, found between a VH (conventional antibodies) and Vab (heavy-chain only antibodies of camelid and shark) (see below) at the hypervariable regions. Camelid Vab and shark V-NAR domains each display surface loops which are larger than for conventional murine and human IgGs, and are able to penetrate cavities in target antigens, such as enzyme active sites and canyons in viral and infectious disease biomarkers [Proc. Natl. Acad. Sci. USA., 101, 12444 (2004); Proteins 55, 187 (2005)]. In human and mouse the VH loops are folded in a limited number of canonical structures. In contrast, the antigen binding loop of Vab possess many deviations of these canonical structures that specifically bind into such active sites, therefore, represent powerful tool to modulate biological activities [K. Decanniere et al., Structure 7, 361 (2000)]. The high incidence of amino acid insertions or deletions, in or adjacent to first and second antigen-binding loops of Vab will undoubtedly diversify, even further, the possible antigen-binding loop conformations.

Though there are structural differences between camelid and shark parent heavy-chain antibodies, the antigen-antibody binding domains, Vab and V-NAR, respectively, are similar. The chemical and/or protease digestion of camelid and shark, antibodies results in Vab and V-NAR domains, with similar binding affinities to the target antigens [Nature Biotech, 23, 1126 (2005)].

Other structural differences are due to the hydrophilic amino acid residues which are scattered throughout the primary structure of Vab domain. These amino acid substitutions are, for example, L45R, L45C, V37Y, G44E, and W47G. Therefore, the solubility of Vab is much higher than the Fab fragment of conventional mouse and human antibodies.

Another characteristic feature of the structure of camelid Vab and shark V-NAR is that it often contains a cysteine residue in the CDR3 in addition to cysteines that normally exist at positions 22 92 of the variable region. The cysteine residues in CDR3 form S—S bonds with other cysteines in the vicinity of CDR1 or CDR2 [Protein Engineering, 7, 1129 (1994)]. CDR1 and CDR2 are determined by the germline V gene. They play important roles together with CDR3 in antigenic binding [Nature Structural Biol., 9, 803 (1996); J. Mol. Biol., 311, 123 (2001]. Like camelid CDR3, shark also has elongated CDR3 regions comprising of 16-27 amino acids residues [Eur. J. Immunol., 35, 936 (2005)].

The germlines of dromedaries and llamas are classified according to the length, of CDR2 and cysteine positions in the V region [Nguyen et al., *EMBO J.,* 19, 921 (2000); Harmsen et al., Mol. Immun., 37, 579 (2000)].

Immunization of camelids with enzymes generates heavy-chain antibodies (HCAb) significant proportions of which are known to act as competitive enzyme inhibitors that interact with the cavity of the active site [M. Lauwereys et al., *EMBO, J.* 17, 3512 (1998)]. In contrast, the conventional antibodies that are competitive enzyme inhibitors cannot bind into large cavities on the antigen surface. Camelid antibodies, therefore, recognize unique epitopes that are out of reach for conventional antibodies.

Production of inhibitory recombinant Vab that bind specifically into cavities on the surface of variety of enzymes, namely, lysozyme, carbonic anhydrase, alfa-amylase, and beta-lactamase hay been achieved [M. Lauwereys, et al., *EMBO, J.* 17, 3512 (1998)]. Hepatitis C protease inhibitor from the camelised human VH has been isolated against an 11 amino. Eng. acid sequence of the viral protease [F. Martin et al., *Prot,* 10, 607 (1997)].

SUMMARY OF THE INVENTION

A. Single-Domain Heavy-Chain Only Antibodies and Peptide Compositions Thereof

The present invention is intended to meet a large unmet medical need for non-invasive diagnosis and treatment of diseases of the central nervous system (CNS). In a first aspect, the present invention teaches peptide compositions of camelid and/or shark single-domain heavy-chain only antibodies and their synthetic peptide composition analogs for breaching the blood-brain barrier (BBB) and cell membranes for diagnosing and/or treating human diseases, including but not limited to, diseases of the central nervous system (CNS) and cancer. FIG. 2 presents the peptide composition structures.

This invention covers single-domain antibodies, and their synthetic peptide composition analogs cross the BBB into the central nervous system and pharmaceutically acceptable formulations of the same. Their general configuration is shown by structures 1 and 2 in FIG. 2. Each structure in FIG. 2 contains one or two Vab domains, and each Vab domain is derived from an antigen-sdAb of camelid (Vab), shark (V-NAR), or combinations thereof.

B. Production of Single-Domain Antibodies

In a second aspect, the invention is also how single-domain antibodies of structures 1 and 2 from FIG. 2 can be produced from the serum of camelids or sharks immunized by an immunogen involved in a CNS disease-causing process. These immunogens can be produced by chemical synthesis and conjugation to BSA or KLH for immunization, or through recombinant DNA technology.

1. Cloning the Single Heavy-Chain from Single-Domain Antibodies

The invention in which the single heavy-chain from a single-domain antibody can be Produced by the techniques of the recombinant DNA technology involving isolation of peripheral blood lymphocytes, extracting total mRNA, reverse transcription to cDNA encoding the peptide composition 2a (FIG. 2, Structure 2, Tables 2-6, variant; R1=1, R2=4, R3=2, L1=1, L2=1, R4=1, R5=1, X=1, Y=1), amplification of the cDNA by PCR, cloning in an appropriate vector, recovering and sequencing the cloned cDNA, cloning the sequenced fragment in a phase vector, transforming the host *E. coli* cells, and purifying the expressed protein, followed by ELISA and Western blot analysis.

The invention in which the PCR primers are represented by SEQ ID NO: 1 and SEQ ID NO: 2.

```
5'---------------------------3'
                                (SEQ ID NO: 1)
CAG GTT CAG CTT GTT GCT TCT GGT (SEQ ID NO: 2)
TTT ACC AGG AGA AAG AGA AAG
```

The invention in which a second round of PCR is done with primers containing built in restriction sites such as Xho and Not1 compatible with commercially available cloning vectors such as SEQ ID NO: 3 and SEQ ID NO: 4.

```
5'---------------------------------3'
                                   (SEQ ID NO: 3)
CTCGAG-CAG GTT CAG CTT GTT GCT TCT GGT (SEQ ID NO: 4)
GCGGCCGC-TTT ACC AGG AGA AAG AGA AAG
```

The invention in which cDNA sequence encoding the single heavy-chain of camelid antibody 2a is represented by the Camelid heavy-chain of single-domain antibody in SEQ ID NO: 5. The lower-case letters are nucleotides at variable positions.

```
                                             (SEQ ID NO: 5)
5'--Variable Antigen-Binding Domain (Vab)------3'
    (1) CAG GTT CAG CTT GTT GCT TCT GGT GGT GGC TCT
        GTT CAG GCT GGT GGT TCT CTT CGT CTT
   (61) TCT TGT GCT GCT TCT GGT TAT ACT TTT TCT TCT
        TAT CCT ATG ggt tgg TAT CGT ggt gct
  (121) CCT ggt AAA GAA tgt GAA CTT TCT gct CGT ATT
        TTT TCT GAT ggt TCT gct AAT TAT gct
  (181) GAT TCT GTT AAA ggt CGT TTT act ATT TCT CGT
        GAT AAT gct gct AAT act gct TAT CTT
  (241) ggt ATG GAT TCT CTT AAA CCT GAA GAT act gct
        GTT TAT TAT tgt gct gct ggt CCT ggt
  (301) TCT ggt AAA CTT GTT GTT gct ggt CGT act tgt
        TAT ggt CCT AAT TAT TGG ggt ggc ggt
  (361) act CAG GTT act GTT TCT TCT (381)

Hinge-Region (HR)
  (382) GAA CCT AAA ATT CCT CAG CCT CAG CCT AAA CCT
        CAG CCT CAG CCT CAG CCT CAG CCT AAA
  (442) CCT CAG CCT AAA CCT GAA CCT GAA tgt act tgt
      CCT AAA tgc CCT (486)

Constant Domain-2 (CH2)
  (487) gct CCT CCT GTT gcc ggc CCT TCT GTT TTT CTT
        TTT CCT CCT AAA CCT AAA GAT act CTT
  (547) ATG ATT TCT CGT act CCT GAA GTT act tgt GTT
        GTT GTT GAT GTT TCT cat GAA GAT CCT
  (607) GAA GTT CAG TTT AAT TGG TAT GTT GAT ggt GTT
        GAA GTT cat AAT gcc AAA act AAA CCT
  (667) CGT GAA GAA CAG TTT AAT TCT act TTT CGT GTT
        GTT TCT GTT CTT act GTT GTT cat CAG
  (727) GAT TGG CTT AAT ggt AAA GAA TAT AAA tgt AAA
        GTT TCT AAT AAA ggt CTT CCT gct CCT
  (787) ATT GAA AAA act ATT TCT AAA act AAA (813)

Constant Domain-3 (CH3)
  (814) ggc CAG CCT CGT GAA CCT CAG GTT TAT act CTT
        CCT CCT TCT CGT GAA GAA ATG act AAA
  (874) AAT CAG GTT TCT CTT act tgt CTT GTT AAA ggt
        TTT TAT CCT TCT GAT ATT GTT GAA TGG
  (934) GAA TCT AAT ggc CAG CCT GAA AAT AAT TAT AAA
        act act CCT CCT ATG CTT GAT TCT GAT
  (994) ggt TCT TTT TTT CTT TAT TCT AAA CTT act GTT
        GAT AAA TCT CGT TgG CAG CAG ggt AAT
 (1054) GTT TTT TCT tgt TCT GTT ATG cat GAA gct CTT
        cat AAT cat TAT act CAG AAA TCT CTT
 (1114) TCT CTT TCT CCT ggt AAA (1131)
```

More specifically, the invention in which the immunogen is derived from, amyloid-peptide-42 (Aβ-42) (SEQ ID: 6), a constituent of amyloid-plaque found in the brain of Alzheimer's patients.

```
                                          (SEQ ID NO: 6)
D A E F R H D S G Y E V H H Q K L V F F A E D V G
S N K G A I I G L M V G G V V I A
```

Still more specifically, the immunogen is one of the following peptide-sequences derived from the Aβ1-42 peptide:

```
                                          (SEQ ID NO: 7)
D A E F H R D S G Y E V H H Q K L V F F A E D V G
S N K G A I I G L M C (SEQ ID NO: 8)
C D A E F H R D S G Y E V H H Q K (SEQ ID NO: 9)
C E D V G S N K G A I I G L M (SEQ ID NO: 10)
D A E F H R D S G Y E V H H Q K
```

2. Target Biomarkers for Single-Domain Antibodies

The invention, wherein the camelid, shark, or a combination thereof single-domain antibody configuration 1 and 2 in FIG. 2 are generated from camelids and/or sharks immunized with immunogen(s) selected from the group of proteins or their metabolic products implicated in neurodegenerative diseases, including hot not limited to, proteins described below.

Alzheimer's Disease (AD) Biomarkers.

Aβ, Tau protein, Tau-kinases (tyrosine kinase Fyn, glycogen synthase kinase 3 (GSK-3), cyclin-dependent protein-kinase-5, casein kinase-1, protein kinase-A, protein kinase-C, calcium and calmodulin-dependent protein-kinase-II, MAPK), ApoE4, beta-secretase, gamma-secretase, translocase of the outer membrane (TOM), TDP43, ApoE4, c-terminal of ApoE4, GSK-3, acetylcholinesterase, NMDA (N-methyl-D-aspartate) receptor, APP (amyloid precursor protein), or ALZAS.

Parkinson's Disease (FD) Biomarkers.

Alpha-synuclein (Natural and mutant), LRRK2 (Natural and mutant), Parkin, DJ-1, Pink1, or Synphilin.

Multiple Sclerosis (MS) Biomarkers.

VIP (vasoactive intestinal peptide), PACAP (pituitary adenylate cyciase-activatlug peptide), factor H, NF-L (neurofilament-light chain), NF-H (neurofilament-heavy chain), Tau, Aβ-42, Antitubulin, NSE (neuron-specific enolase), Apo-E, GAP-43 (growth-associated protein 43), 24S-OH-chol (24S-hydroycholesterol), Protein 14-3-3, sVCAM (solublevascular cell adhesion molecule), or sPECAM (soluble platelet endothelial cell adhesion molecule).

Glioblastoma Biomarkers.

EGFR, HER2, PDGF (platelet-derived growth factor), FGFR (fibroblast growth factor receptor), STATs (signal transducers and activators of transcription), GDHF (glial cell-line derived neurotrophic factor), mTOR (mammalian target of rapamycin), VEGF (vascular endothelial growth factor), TGF-beta (transforming growth factor beta), P13K, Ras, Raf, MAPK, AKT (aka: Protein Kinase B), MAPK, TIMP1, CD133, SPP1 (secreted phosphoprotein 1), TP53, PTEN, TMS1, IDH1, NF1, or IL-10.

Huntington's Disease Biomarkers.

H2aFY, mutant HTT, 8-Hydroxy-2-deoxy-guanosine, Copper-Zn Superoxide Dismutase, A2a receptor, transglutaminase, or poly-glutamine.

In preferred embodiments, the target biomarker to which the inventive polypeptides specifically bind is an extracellular protein within the CNS or is a membrane-bound protein for which the antigenic epitope is accessible by the polypeptide from the extracellular space (e.g., an extracellular domain of a membrane-bound protein).

3. Camelid Single-Chain Aβ-sdAb Sequence

The present inventions are based upon the discovery that a single domain heavy chain-only antibody derived from camelids and/or shark retains antigen binding activity and is capable of crossing the blood-brain-barrier of mammals. In its simplest form, the present are based on compositions and methods for using native or modified camelid and/or shark single domain, polypeptides derived from, or based on, the native heavy chain-only antibodies. For example, the native single domain polypeptides of camelid heavy chain-only antibodies have the general form of: Vab-hinge region (HR)-CH2-CH3, as illustrated in FIG. 16. In some embodiments, the Vab domain may be all or a portion of the native Vab domain provided that the Vab domain retains its antigen binding capacity. In other embodiments, the hinge region may be all or a portion of the native hinge region and/or may be a non-peptide chemical linker as described herein. The CH domains may be the CH domains native to the species of the Vab domain, or fragments thereof, or may be derived from another species, or fragments thereof. For example, a single domain heavy chain polypeptide may have a camelid Vab domain and HR, one or more CH domains derived from a human IgG and/or one or more CH domains derived, from shark IgG either with or without one or more of the camelid CH domains. Optionally, the single domain heavy chain only polypeptide may further comprise a peptide and/or non-peptide linker and another moiety (e.g., ligand or a second single domain heavy chain polypeptide, or CH domain from another species such as camelid, shark, or human.

The invention in which the amino-acid sequence of the single polypeptide heavy-chain is represented by the amino acid sequence of peptide composition 2a (SEQ ID NO: 11, the amino acid sequence of a camelid single-domain heavy-chain only antibody), which is a single chain from peptide composition 1a (FIG. 2, structure 1, R=1) a camelid antibody

```
Amino Acid Sequence of Camelid Single-Domain
Heavy-Chain Only Antibody
(Peptide Composition 2a, (SEQ ID: 11)
Variable Antigen-Binding Domain (Vab)
   (1) QVQLVASGGG SVQAGGSLRL SCAASGYTFS SYPMGWYRGA

PGKECELSAR IFSDGSANYA DSVKGRFTIS RDNAANTAYL

GMDSLKPEDT ADYYCAAGPG SGKLVVAGRT CYGPNYWGGG

TQVTVSS (127)

Hinge-Region (HR)
 (128) EPK IPQPQPKPQP QPQPQPKPQP KPEPECTCPK CP (162)

Constant Region 2
 (163) APPVAGPSVF LFPPKPKDTL MISRTPEVTC VVVDVSHEDP

EVQFNWYVDG VEVHNAKTKP REEQFNSTFR VVSVLTVVHQ

DWLNGKEYKC KVSNKGLPAP IEKTISKTK (272)

Constant Region 3
 (273) G QPREPQVYTL PPSREEMTKN QVSLTCLVKG FYPSDISVEW

ESNGQPENNY KTTPPMLDSD GSFFLYSKLT VDKSRWQQGN

VFSCSVMHEA LHNHYTQKSL SLSPGK (378)
```

C. Peptide Composition of Structure 1 in FIG. 2

The invention in which variable antigen-binding domains of heavy-chain single-domain shark and/or camelid antibodies axe linked together through a constant domain CH2 of human IgG camelid IgG, or shark IgNAR which is linked to a constant domain CH3 of human IgG, camelid IgG or shark IgNAR to form bivalent Vab domains of single-domain heavy-chain only antibody of the general structure of structure 1 in FIG. 2. Exemplary variants of the "R" group in structure 1 from FIG. 2 are listed in Table 1.

TABLE 1

Variants of R from Structure 1 in FIG. 2

| R Variant | Description |
|---|---|
| 1 | H |
| 2 | a detectable label |
| 3 | a short-lived radioisotope including, but not limited to, as $^{123}$I, $^{124}$I, $^{77}$Br, $^{67}$Ga, $^{97}$Ru, $^{99}$Tc, $^{111}$In or $^{89}$Zr introduced either using a reagent such as $^{124}$I-Bolton Hunker or $^{124}$I-SIB or a metal chelator |
| 4 | a long-lived radionisotope including, but not limited to, as $^{131}$I, $^{211}$At, $^{32}$P, $^{47}$Sc, $^{67}$Cu, $^{186}$Re, $^{188}$Re, $^{140}$Ia, $^{111}$Ag, $^{90}$Y, $^{105}$Rh, $^{109}$Pd, $^{199}$Au for therapeutic applications, with or without a labeling entity, such as a bifunctional reagent (Bolton Hunker or SIB reagent) or a bifunctional chelating agent between the polypeptide and the radionuclide |
| 5 | NH—CO—$C_6H_4$-Iodine-124, 125, 111, 113, 112, or 131 |
| 6 | a fluorophore including, but no limited to, FITC and other fluorescein derivatives, Texas-Red, rhodamine, Cy3, Cy5, thioflavin dyes, AlexaFluor, 1,4-Bis(4'-aminostyryl)-2-dimethoxy-benzene (BDB: Formula 1a), [5'-(4-methoxyphenyl)[2,2'-bithiophen]-5yl]methylene]-propanedinitrile (Formula 1b) [5'-(4-methoxyphenyl)[2,2'-bithiopehen]-5yl]-aldehyde (Formula 1c), or fluorophore analogs thereof |
| 7 | a therapeutic agent, toxin, hormone, or peptide |
| 8 | a protein, such as an enzyme |
| 9 | an antibody, the Fc region of IgGs, sd-insulin-Ab 1 (Structure 1 in FIG. 2) sd-insulin-Ab 2 (Strutcture 2 in FIG. 2), sd-transferrin-Ab 1, or sd-transferrin-Ab 2 |
| 10 | biotin, digoxigenin, avidin, or streptavidin |
| 11 | fused or covalently bound to a protein that recognizes or binds to the receptors on endothelial cells that form the BBB, including, but not limited to, insulin, transferrin, Apo-B, Apo-E, such as Apo-E4, Apo-E Receptor Binding Fragment, FC5, FC44, substrate for RAGE (receptor for advanced glycation end products), substrate for SR (macrophage scavenger receptor), substrate for AR (adenosine receptor), RAP (receptor-associated protein), IL17, IL22, or protein analogs thereof |
| 12 | nucleic acids including, but not limited to, a gene, vector, si-RNA, or micro-RNA |
| 13 | covalently bound to biodegradable nanoparticles, such as polyalkylcyanoacrylate nanoparticles (PACA-NPs), wherein the PACA nanoparticles are synthesized from a substituted surfactant, wherein the surfactant is dextran, polyethylene glycol, heparin, and derivatives thereof; wherein the substitution is that of an amino group, thiol group, aldehydic group, —CH2COOH group, with or without appropriate protection, for subsequent covalent conjugation of the said polypeptide |

Variants in Table 1 include mutants of the peptides, proteins, and nucleic acid sequences. The variants may include a bifunctional linking moiety including, but not limited to, peptides, such as glycyl-tyrosyl-glycyl-glycyl-arginine (SEQ ID NO: 12); tyramine-cellobiose (Formula 2); Sulfo-SMCC; NHS—($CH_2$—$CH_2$—O)n-Mal (wherein n=1-100, NHS stands for N-hydroxysaccinimide, and Mal stands tor maleimido group); Succinimidyl-3 (4-hydroxyphenyl)-propionate; (3-(4-hydroxyphenyl) propionyl-carbonylhydrazide; EDTA (ethylenedinitrilotetraaceticacid); DTPA (diethylenetriaminepentaacetic acid) and DTPA analogs (Formula 3); NTA (N,N',N"-triacetic acid); chelating agents such as desferroxamine (DFA) and bifunctional linker analogs thereof. EDTA derivatives include 1-(p-bromoacetamidophenyl)-EDTA, 1-(p-benzenediazonium)-EDTA, 1-(p-bromoacetaminodophenyl)-EDTA, 1(p-bromacetaminodophenyl)-EDTA, or 1-(p-succinimidyl-benzyl)-ETDA.

Formula 1

Fluorophores that can be conjugated to the peptide compositions

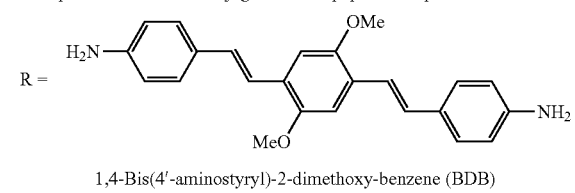

1,4-Bis(4'-aminostyryl)-2-dimethoxy-benzene (BDB)

R = 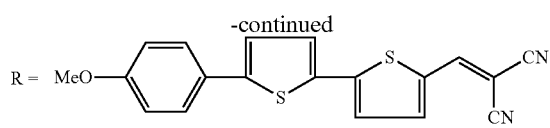

[5'-(4-methoxyphenyl)[2,2'-bithiophen]-5yl]
methylene]-propanedinitrile

R = 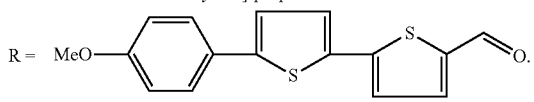

[5'-(4-methoxyphenyl)[2,2'-bithiophen]-5yl]aldehyde

Formula 2

Tyramine-Cellobiose (TCB)

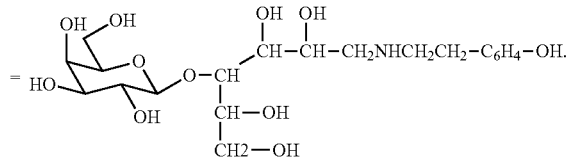

Formula 3

Diethylenetriaminepentaacetric acid (DPTA) derivatives

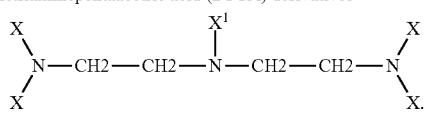

$X = X^2 = CH_2COOH$ (DTPA)

$X = CH2—COOH$, $X^1 = X^2 —C6H4—CH2$

Wherein $X^2$ = N-Hydroxy-Succinimide;
 = 1-(p-isothiocyanatobenzy);
 = 1-(p-bromoacetamidobenzyl)

D. Peptide Compositions of Structure 2 in FIG. 2

The invention in which one or more variable antigen-binding domains (from camelid Vab, shark V-NAR, or a combination thereof) of heavy-chain polypeptides are chemically or enzymatically linked together through a hinge region (HR), a non-peptidyl linker (such as a PEG linker), or combination thereof, to a constant domain CH1, CH2 or CH3 of human IgG, CH2 or CH3 camelid IgG, or CH1, CH2, CH3, CH4, or CH5 shark IgNAR to form a bivalent Vab domains of single-domain heavy-chain only antibodies of the general structure of structure 2 in FIG. 2. Exemplary variants of the "R1," "R2," "R3," "L1," "L2," "R4," "R5," "X," and "Y" groups in structure 1 from FIG. 2 are listed in Tables 2-6.

TABLE 2

Variants of R1 or R2 from Structure 2 in FIG. 2

| R1 or R2 Variant | Description |
|---|---|
| 1 | All or a part of a variable antigen-binding domain of a single-domain antibody (Vab-sdAb) for an antigen, where the Vab is derived from camelid Vab, shark V-NAR, or a combination thereof |
| 2 | a Constant domain 1 (CH1) of Hu-IgG |
| 3 | a Constant domain 2 (CH2) of Hu-IgG |
| 4 | a Constant domain 3 (CH3) of Hu-IgG |
| 6 | a Constant domain 2 (CH2) of camelid-IgG |
| 7 | a Constant domain 3 (CH3) of camelid-IgG |
| 8 | a Constant domain 1 (CH1) of shark-IgNAR |
| 9 | a Constant domain 2 (CH2) of shark-IgNAR |
| 10 | a Constant domain 3 (CH3) of shark-IgNAR |
| 11 | a Constant domain 4 (CH4) of shark-IgNAR |
| 12 | a Constant domain 5 (CH5) of shark-IgNAR |

Variants include mutants of the constant domains. At least R1 or R2 = 1.

TABLE 3

Variants of R3 from Structure 2 in FIG. 2

| R3 Variant | Description |
|---|---|
| 1 | a Constant domain 1 (CH1) of Hu-IgG |
| 2 | a Constant domain 2 (CH2) of Hu-IgG |
| 3 | a Constant domain 3 (CH3) of Hu-IgG |
| 4 | a Constant domain 2 (CH2) of camelid-IgG |
| 5 | a Constant domain 3 (CH3) of camelid-IgG |
| 6 | a Constant domain 1 (CH1) of shark-IgNAR |
| 7 | a Constant domain 2 (CH2) of shark-IgNAR |
| 8 | a Constant domain 3 (CH3) of shark-IgNAR |
| 9 | a Constant domain 4 (CH4) of shark-IgNAR |
| 10 | a Constant domain 5 (CH5) of shark-IgNAR |

Variants include mutants of the constant domains.

TABLE 4

Variants of L1 or L2 from Structure 2 in FIG. 2

| L1 or L2 Variant | Description |
|---|---|
| 1 | a hinge-region of a sdAb comprising of up to 35 amino acids, wherein the amino acid sequence is EPKIPQPQPKPQPQPQPQPKPQPKPEPECTCPKCP (SEQ ID NO: 13) or a portion thereof |
| 2 | a linker up to 20 nm long in length, wherein the linker is comprised of polyethylene glycol $(CH_2—CH_2—O))_n$ and n = 5-70 |
| 3 | a linker comprising from a group consisting of NHS-$(CH_2—CH_2—O)$n-Mal, wherein n = 1-100, NHS stands for N-hydroxysuccinimide, and Mal stands for maleimido group; Succinimidyl-3 (4-hydroxyphenyl)-propionate; (3-(4-hydroxyphenyl) propionyl-carbonylhydrazide; EDTA (ethylenedinitrilotetraaceticacid), DTPA (diethylenetriaminepentaacetic acid), or NTA (N,N',N"-triacetic acid) |
| 4 | alkoxy, alkyl, peptidyl, nucleic acid, unsaturated aliphatic chains or combinations thereof |

Variants include mutants of the constant domains.

TABLE 5

Variants of R4 or R5 from Structure 2 in FIG. 2

| R4 or R5 Variant | Description |
|---|---|
| 1 | H |
| 2 | a detectable label |
| 3 | a short-lived radioisotope including, but not limited to, as $^{123}I$, $^{124}I$, $^{77}Br$, $^{67}Ga$, $^{97}Ru$, $^{99}Tc$, $^{111}In$ or $^{89}Zr$ introduced either using a reagent such as $^{124}I$-Bolton Hunker or $^{124}I$-SIB or a metal chelator |
| 4 | a long-lived radionisotope including, but not limited to, as $^{131}I$, $^{211}At$, $^{32}P$, $^{47}Sc$, $^{67}Cu$, $^{186}Re$, $^{188}Re$, $^{140}Ia$, $^{111}Ag$, $^{90}Y$, $^{105}Rh$, $^{109}Pd$, or $^{199}Au$ for therapeutic applications, with or without a labeling entity such as a bifunctional reagent (Bolton Hunter or SIB reagent) or a bifunctional chelating agent between the polypeptide and the radionuclide |
| 5 | NH—CO—$C_6H_4$-Iodine-124, 125, 111, 113, 112, or 131 |
| 6 | a fluorophore including, but no limited to, FITC and other fluorescein derivatives, Texas-Red, rhodamine, Cy3, Cy5, thioflavin dyes, AlexaFluor, 1,4-Bis(4'-aminostyryl)-2-dimethoxy-benzene (BDB; Formula 1a), [5'-(4-methoxyphenyl)[2,2'-bithiophen]-5yl]methylene]-propanedinitrile (Formula 1b) [5'-(4-methoxyphenyl)[2,2'-bithiopehen]-5yl]-aldehyde (Formula 1c), or fluorophore analogs thereof |
| 7 | a therapeutic agent, toxin, hormone, or peptide |
| 8 | a protein, such as an enzyme |
| 9 | an antibody, the Fc region of IgGs, sd-insulin-Ab 1 (Structure 1 in FIG. 2) sd-insulin-Ab 2 (Structure 2 in FIG. 2), sd-transferrin-Ab 1, or sd-transferrin-Ab 2 |
| 10 | biotin, digoxegenin, avidin, streptavidin |
| 11 | fused or covalently bound to a protein that recognizes or binds to the receptors on endothelial cells that form the BBB, including, but not limited to, insulin, transferrin, Apo-B, Apo-E, such as Apo-E4, Apo-E Receptor Binding Fragment, FC5, FC44, substrate for RAGE (receptor for advanced glycation end products), substrate for SR (macrophage scavenger receptor), substrate for AR (adenosine receptor), RAP (receptor-associated protein), IL17, IL22, or protein analogs thereof |
| 12 | nucleic acids including, but not limited to, a gene, vector, si-RNA, or micro-RNA |
| 13 | covalently bound to biodegradable nanoparticles, such as polyalkylcyanoacrylate nanoparticles (PACA-NPs), wherein the PACA nanoparticles are synthesized from a substituted surfactant, wherein the surfactant is dextran, polyethylene glycol, heparin, and derivatives thereof; wherein the substitution is that of an amino group, thiol group, aldehydic group, —CH2COOH group, with or without appropriate protection, for subsequent covalent conjugation of the said polypeptide |

Variants include mutants of the peptides, proteins, and nucleic acid sequences. The variants may include a bifunctional linking moiety including, but not limited to, peptides, such as glycyl-tyrosyl-glycyl-glycyl-arginine (SEQ ID NO: 12); tyramine-cellobiose (Formula 2); NHCO—($CH_2$—$CH_2$—O)n (wherein n=1-100, 5-75, 5-50, 5-25, or 10-20), Sulfo-SMCC; NHS—($CH_2$—$CH_2$—O)n-Mal (wherein n=1-100, 5-75, 5-50, 5-25, or 10-20, NHS stands for N-hydroxysuccinimide, and Mal stands for malemido group); Succinimidyl-3 (4-hydroxyphenyl)-propionate; (3-(4-hydroxyphenyl) propionyl-carbonylhydrazide; EDTA (ethylenedinitrilotetraaceticacid); DTPA (diethylenetriamiepentaacetic acid) and DTRA analogs (Formula 3); NTA (N,N'N"-triacetic acid); chelating agents such as desferroxamine (DFA) and bifunctional linker analogs thereof. EDTA derivatives include 1-(p-bromoacetamidophenyl)-EDTA, 1-(p-benzenediazonium)-EDIA, 1-(p-bromoacetamindophenyl)-EDTA, 1(p-isothiocyanatobenzyl)-EDTA, or 1-(p-succinimidyl-benzyl)-EDTA.

TABLE 6

Variants of X or Y from Structure 2 in FIG. 2

| X or Y Variant | Description |
|---|---|
| 1 | a bifunctional peptidyl, alkyl-, alkoxy-, aromatic, nucleotide linker or a combination thereof including any of the foregoing variants of L. |

E. Peptide Nanoparticle Compositions of Structures 1 and 2 in FIG. 2

Any of the polypeptides of the invention, including the structures 1 or 2 in FIG. 2 and the single domain polypeptides, may be covalently linked to biodegradable nanoparticles, which are comprised of a surfactant, polymerizable monomeric entity, wherein surfactant is carrying a functionally active group such as amino group, aldehyde group, thiol group, —CH2-COOH group, succinic anhydride group or other group capable of forming a covalent bond between the nanoparticles and the peptide compositions. The following examples exemplify these embodiments but the principles and disclosure may be applied to any of the polypeptides disclosed herein.

Structure 1 in FIG. 2 (at R) and structure 2 in FIG. 2 (at R4 and/or R5) may be conjugated to biodegradable nanoparticles. Wherein the nanoparticles are synthesized by the chemical reaction of biodegradable alkylcyanoacrylate with a substituted polymer such as dextran, heparin, polyethylene glycol, and the like; wherein the substitution is that of a group, free or protected, capable of forming a covalent bond with the native and/or modified, single-domain antibody.

Wherein, in Formula 4, X=—NH, S, CHO, phosphate, thiophosphate, or phosphonate; and wherein, in Formula 4, Y=a peptide composition of structure 1 in FIG. 2 or a peptide composition 2 in FIG. 2, or combinations and variants of structures 1 and 2.

Peptide Nanoparticle Compositions.

Formula 4

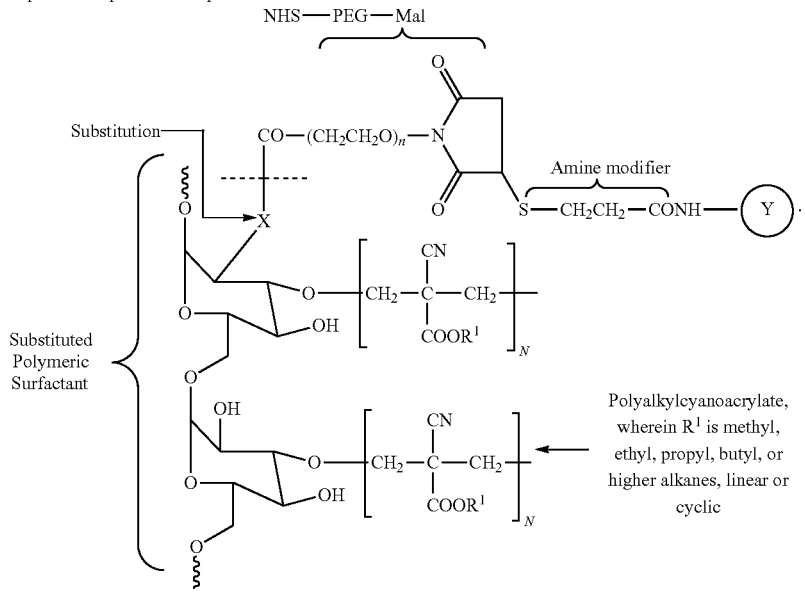

Amino-Dextran-coated-Polyalkylcyanoacrylate-Nanoparticles with covalently bound single-domain antibody

F. Methods for Treatment

Any of the polypeptides of the invention, or derivatives thereof, disclosed herein may be used for treating neurologic diseases, including neurodegenerative diseases in a mammal (e.g., a human). In one embodiment, the polypeptides are administered to a subject in need thereof (e.g., a subject diagnosed as having or at risk of developing a neurologic disease) in an amount sufficient to treat or prevent that neurologic disease, wherein the polypeptide specifically binds to a target biomarker.

In a related method, the invention provides a method for reducing the biological activity (e.g., amount) of a target biomarker in the central nervous system (CNS) of a subject by administering a polypeptide of the invention according to the methods disclosed herein.

Neurologic diseases amenable to treatment or prevention according to these methods include, for example, Alzheimer's disease, Parkinson's disease, multiple sclerosis, Huntington's disease, and cancers of the central nervous system such as glioblastoma.

The polypeptides are administered in an amount and duration sufficient treat or prevent the neurological disease. For example, the polypeptides may be administered one or twice a day, or more frequently, about once a week, or about once a month. The polypeptides may be administered as a single (one-time) treatment or for a duration of a week, a month, two months, six months, one year, or more, or for the lifetime of the subject. The polypeptides may be administered as a unitary dosage (e.g., a dosage administered over a discrete duration of time) or by continuous infusion. Administered doses of the polypeptide (i.e., "an amount sufficient") may be about 1 mg, 2 mg, 5 mg, 10 mg, 25 mg, 50 mg, 100 mg or more per day.

In preferred embodiments, the amount and/or biological activity of the target biomarker is reduced in the nervous system of the subject following administration of the polypeptide.

G. Methods and Diagnosis

Any of the polypeptides of the invention, or derivatives thereof, disclosed herein may be used for diagnosing a subject (e.g., a human) as having, or at risk of developing, a neurologic disease. One diagnostic method comprises (i) administering an inventive polypeptide comprising a detectable label to the subject, wherein the polypeptide binds to a target biomarker, (ii) waiting for a time sufficient for the polypeptide to permeate the blood-brain-barrier and bind to the target biomarker, if present, (iii) determining the presence or amount of detectable label within the central nervous system (CNS) and (iv) identify the subject as having, or at risk of developing, the neurologic disease when the measured amount of the target biomarker is different from the measured amount of the target biomarker in a subject or population of subjects known to be either disease-free or not at risk of developing the disease. In some embodiments of this method, an increase or a decrease in the amount of target biomarker relative to the subject or population of subjects known to be either disease-free or not at risk of developing the disease indicates that the tested subject either has the disease or is at risk of developing the disease.

Another diagnostic method comprises (i) at a first time, administering an inventive polypeptide comprising a detectable label to the subject and obtaining a first measurement of the amount of the detectable label within the CNS of the subject, wherein the polypeptide binds to a target biomarker; (ii) at a second time, administering an inventive polypeptide comprising a detectable label to the subject and obtaining a first measurement of the amount of the detectable label within the CNS of the subject; and (iii) comparing the amount of detectable label within the CNS of the subject at the second time to the amount of detectable label within the CNS of the subject at the first time, wherein a change in the amount of detectable label at the second time relative to the first time indicates that the subject has, or is at risk of developing, the neurological condition. In some embodiments of this method, an increase or a decrease in the amount of target biomarker at the second time relative to the first time indicates that the tested subject either has the disease or is at risk of developing the disease. The duration of time between the first measurement and the second measurement can be any time that is convenient and appropriate for the disease under investigation. For example, the time may be at least about one day, one week, one month, two months, three months, six months, one year, two years, three years, five years, or more.

In another embodiment, the invention provides a method for labeling one or more targets in the CNS of a vertebrate, such as a mammal or a human, using any of the foregoing methods, wherein the polypeptide comprises a detectable label.

In some embodiments of the foregoing diagnostic methods, the target biomarker is amyloid beta and the neurologic disease is Alzheimer's disease. In other embodiments, the target biomarker is LRRK2 and the neurologic disease is Parkinson's disease.

In any of the foregoing methods, it is contemplated that the presence or amount of detectable label detected or measured in the CNS of a subject is indicative of the presence or amount target biomarker in the CNS of that subject.

H. Use of Single-Domain Heavy Chain Only Antibodies and Derivatives as a CNS Shuttle Any of the polypeptides of the invention, or derivatives thereof, disclosed herein may be used to carry other diagnostic or therapeutic molecules ("shuttled molecules") into the CNS accordingly to the methods set forth above. The shuttled molecules themselves may be capable of crossing the blood-brain-barrier, albeit on a limited basis, or may be impermeate to the blood-brain-barrier. Thus, higher CNS levels of the shuttled molecules may be achieved by attaching such molecules to the inventive polypeptides according to the methods described herein. In some embodiments, the shuttled molecule is a diagnostic agent (e.g., a detectable label) or a therapeutic agent for treating a cancer or other neurologic disease. In other embodiments, the target biomarker to which the polypeptide binds is present on or near the target cells of interest. For example, when treating or diagnosing a glioblastoma, wherein the shuttled molecule is a chemotherapeutic agent or imaging agent, respectively, target biomarkers present on glioblastoma cells are preferred. Likewise, when treating Alzheimer's disease or Parkinson's disease, target biomarkers on cholinergic and dompaninergic neurons, respectively, is preferred.

I. Specific Embodiments of Single Domain Heavy Chain Only Antibodies

In any of the foregoing methods and compositions, the following embodiments of the polypeptides are particularly useful. In one embodiment, the polypeptide comprising the formula: Vab-Z-Z' wherein Vab comprises all or a portion of a variable antigen-binding (Vab) domain of a camelid or shark single domain heavy chain antibody, wherein Z comprises all or a portion of a hinge region from an IgG or a linker comprising —NHCO—, wherein Z' comprises a covalent bond or all or a portion of at least one IgG CH domain, and wherein the polypeptide is capable of specifically binding to a target biomarker within the central nervous system (CNS) of the subject;

The polypeptide optionally may further comprise a detectable label including, for example, a radiolabel such as a position-emitting radioisotope.

In one embodiment, the polypeptide contains only a single Vab of a single domain heavy chain antibody lacking light chains. In further embodiments, this polypeptide contains a single camelid Vab covalently attached to a camelid CH2 and/or a camelid CH3 domain. The attachment may be through a hinge region and/or a chemical linker, as defined herein. In a related embodiment, the polypeptide comprises the formula $Vab^1$-$Z^1$-$Z'$-$Z^2$-$Vab^2$, wherein $Vab^2$ independently comprises all or a portion of a variable antigen-binding (Vab) domain of a camelid or shark single domain heavy chain antibody and $Z^2$ independently comprises all or a portion of a hinge region from an IgG (e.g., camelid CH2 and/or a camelid CH3 domain).

In another embodiment, Z comprises a linker Optionally, Z' is covalently attached to a second Vab-Z moiety such that the polypeptide comprises the formula: $Vab^1$-$Z^1$-$Z'$-$Z^2$-$Vab^2$, wherein $Vab^2$ independently comprises all or a portion of a variable antigen-binding (Vab) domain of a camelid or shark single domain heavy chain antibody and $Z^2$ independently comprises all or a portion of a lunge region from an IgG and/or a linker.

In another embodiment, Z comprises all or a portion of a hinge region from an IgG. Optionally, Z' is covalently attached to a second Vab-Z moiety such that the polypeptide comprises the formula: $Vab^1$-$Z^1$-$Z'$-$Z^2$-$Vab^2$, wherein $Vab^2$ independently comprises all or a portion of a variable antigen-binding (Vab) domain of a camelid or shark single domain heavy chain antibody and $Z^2$ independently comprises all or a portion of a hinge region from as IgG and/or a linker.

In another embodiment, Z comprises all or a portion of a hinge region from an IgG and a a linker. Optionally, Z' is covalently attached to a second Vab-Z moiety such that the polypeptide comprises the formula: $Vab^1$-$Z^1$-$Z'$-$Z^2$-$Vab^2$, wherein $Vab^2$ independently comprises all or a portion of a variable antigen-binding (Vab) domain of a camelid or shark single domain heavy chain antibody and $Z^2$ independently comprises all or a portion of a hinge region from an IgG and/or a linker.

In any of the foregoing embodiments, Z' may comprises all or a portion of a human IgG CH domain (e.g., CH1, CH2, and/or CH3), camelid CH domain (e.g., CH2 and/or CH3), and/or shark CH domain (e.g, CH1, CH2, CH3, CH4, and/or CH5).

In any of the foregoing embodiments, suitable chemical linkers include, for example, linkers which contain a PEG moiety such as —$(CH_2CH_2$—$O)_n$— and wherein n=1-100, 2-75, 2-50, or 2-24, (e.g., n is at least 2, 4, 6, 8, 10, 12, 14, 16, 18, 20, 22, or 24). In specific embodiments, the linker comprises —NHCO—$(CH_2CH_2$—$O)_n$—, or —$(C_4H_3NO_2)$—S—$(CH_2)_3$-imidate-, or —CH$(CH_2SH)$—NHCO—, or —NHCO—$(CH_2CH_2$—$O)_n$—$(C_4H_3NO_2)$—S—$(CH_2)_3$-imidate-.

In any of the foregoing embodiments, the polypeptide optionally may be linked to a nanoparticle. In some embodiments, the nanoparticle has a diameter of about 10 nm to about 500 nm, is covalently linked to the nanoparticle via a linker comprising —NHCO— and related linkers described herein, and/or comprises polybutylcyanoacrylate.

By "treatment," when referring to the therapeutic methods of the present invention, is meant administration of a polypeptide in an amount and duration sufficient to ameliorate at least one symptom of the disease. Symptoms that may be ameliorated include clinical symptoms (e.g., tremor in PD or cognitive impairment in AD), anatomical (e.g., slowing or reversing neuronal loss), of biochemical (e.g., reducing the biological activity the target biomarker).

By "prevention" is meant administering a polypeptide in an amount and duration sufficient to slow or halt a pathological change associated with the neurologic disease in a subject identified as being at risk of disease development (i.e., if the subject is asymptomatic and does not otherwise meet the criteria for a positive diagnosis) or disease progression.

By "administration" is meant, the delivery of a polypeptide of the invention to the subject in need thereof in a manner designed to ultimately result in the delivery of that polypeptide to the central nervous system of the subject. Routes of administration may include oral and/or parenteral delivery. Parenteral delivery includes subcutaneous, intravenous, intramuscular, intrathecal, and intraventricular injection.

By "biological activity," when referring to a target biomarker, is meant the physiological activity normally associated with the target biomarker protein. For example, in the case of enzymes, the biological activity refers to the normal catalytic activity of that enzyme. In the case of structural or other proteins lacking a catalytic activity, biological activity refers to the normal functioning of that protein in a cell of the nervous system (e.g., the ability to polymerize with other structural proteins). Biological activity may be reduced by reducing the amount of the target biomarker protein and/or inhibiting the function of the target biomarker protein.

As used herein, "amyloid beta" may refer to the amyloid beta protein itself and/or amyloid plaque including soluble, insoluble, and diffusable amyloid plaques.

By "pharmaceutically acceptable formulation" is meant a formulation suitable for administration to a subject (e.g., a mammal such as a human). Pharmaceutically acceptable formulations generally include a polypeptide of the invention and at least one compatible excipient. Co-formulations with additional therapeutic agents are also contemplated.

By "derived from," when used in reference to the polypeptides of the present invention or individual domains thereof, is meant that the polypeptide or domain has a primary amino acid sequence that is substantially identical to a native polypeptide or domain.

By "substantially identical" is meant a polypeptide or nucleic acid sequence that is at least 75%, 80%, 85%, 90%, 95%, 99%, or 100% identical to a reference sequence (e.g., a naturally-occurring sequence) over the length of comparison which is at least 10, 15, 20, 25, 30, 40, 50, or more monomeric units (e.g., nucleotides, or amino acids) long. In some embodiments, a substantially identical sequence is 100% identical to the reference sequence. In other embodiments, with reference to polypeptides, the sequence is not identical to the reference sequence but contains one, two, three, four, five, or more conservative amino acid substitutions.

BRIEF DESCRIPTION OF THE DRAWINGS

The accompanying drawings, which are incorporated in and constitute a part of this specification, illustrate several aspects described below.

FIG. 7 is a photograph of the immunostaining results of immunohistochemical (IHC) staining of paraffin embedded brain tissues from the APP transgenic mouse (FIG. 7A left upper two frames) and Alzheimer's patient (FIG. 7A lower two frames); with and without primary Aβ-sdAb (FIG. 7A frames), and staining of the same tissues with Thioflavin-S dye (FIG. 7B frames).

FIG. 8 depicts the BBB permeability tests for Aβ-sdAb 1a (FIG. 2, Structure 1 Table 1, Variant: R=1) and peptide composition 2a (single-chain of Aβ-sdAb 1a; FIG. 2, Structure 2, Tables 2-6, variant: R1=1, R2=4, R3=2, L1=1, L2=1, R4=1, R5=1, X=1, Y=1) in mice.

DETAILED DESCRIPTION OF THE PREFERRED EMBODIMENTS

Figure 1:
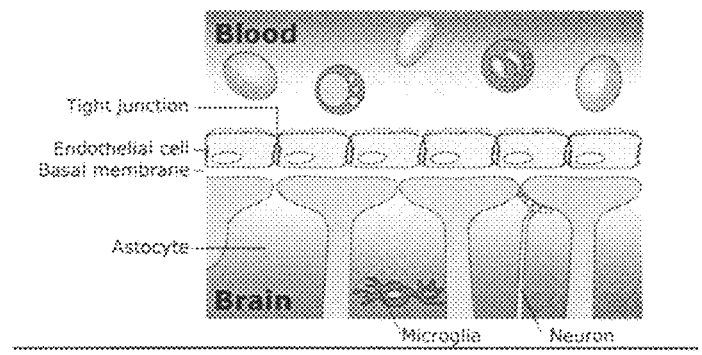
FIG. 1 is a diagram of the right junctions in the endothelial cell membrane that form the barrier between the blood and the brain.

In the following detailed description, reference is made to the accompanying drawings, which form a part thereof. The illustrative embodiments described in the detailed description, drawings and claims are not meant to be limiting. Other embodiments may be utilized, and other changes may be made, without departing from the spirit or scope of the subject matter presented here. The present technology is also illustrated by the examples herein, which should not be construed as limiting in any way.

A. Isolation of Aβ-Single-Domain Antibody 1A (Aβ-SDAB 1A, Structure 1 in FIG. 2)

1. Immunization of Camelids with Aβ1-35 Peptide

All animals (llamas) were treated following NIH guidelines. First, the animals were given a complete physical examination by our veterinarian, Dr. Linda Byer, who also drew some pre-immunization blood. Immunization was then started with $A\beta_{1-35}$ synthetic peptide (200 ug) in Gerbu Pharma Adjuvant (1 ml). One month after the initial priming injection, six biweekly boosters were administered at 200 ug/injection. After the fourth booster, about 20 ml blood was drawn and serum examined for antibody titer with antigen coated 96-well ELISA plate. After immunization, ~200 ml blood was drawn from the animal. Half of the blood was used to isolate single-domain Aβ-antibody (polyclonal) with the methods below in Sections A.2-4. The second half of the blood was used to isolate peripheral blood lymphocytes (PBLs) to prepare total RNA followed by its reverse transcription to cDNA which was then ligated into the phage vector to generate phage-display cDNA library (Section D).

2. Crude Isolation of Aβ-sdAb 1a from Camelid Serum

After immunization, 100 ml from each blood sample drawn was processed to fractionate sdAbs (MW: ~90 KDa) from the classical antibodies (MW: ~160 KDa). Briefly, the serum (~50 ml) was concentrated on an Millipore-Amicon Ultra-15 Concentrator, molecular weight cutoff 50 KDa, by spinning the device at 4000 g, until most of the low molecular weight species passed through the membrane. The thick viscous yellow retentate (~25 ml) was extracted with chloroform (3×25 ml) to remove fatty substances, which had contributed to the viscosity of the retentate. The resulting crude product (2×10 ml) was size fractionated on Superdex-200 (2.5 cm×100 cm) using 1×PBS as eluant. The fractions were monitored by reading $OD_{280}$ on a Beckman DU-640 Spectrophotometer. After examining the fractions on a 12% SDS-PAGE gel, the fractions whose products correspond to the molecular weight of ~90 KDa were pooled, concentrated and the protein concentration was measured by checking its $OD_{280}$.

3. Generation of an Affinity Column for Enrichment of Aβ-sdAb 1a 10 mg of immunogen Aβ1-35, dissolved in 5 ml of conjugation buffer, 0.1 M $NaHCO_3$/0.15M NaCl, pH 8.5, was conjugated with cyanogen-bromide activated Sepharose (2 gm), which had been washed with 200 ml of ice-cold 1 mM HCl. The reaction was allowed to proceed for 2 hours while the resin was allowed to gently rock on a rocket. After centrifugation, the supernatant of the reaction mixture was examined by its $OD_{280}$ reading, which indicated that essentially all of the immunogen had been consumed. The resin was then washed with pH 8.5 conjugation buffer (3×20 ml), and then blocked with 1 M Tris.HCl, pH 8.3 (10 ml), room temperature for 2 hours. After washing the resin with 0.1 M $NaHCO_3$/0.5M NaCl pH 8.5, the resin was washed with 0.1 M sodium citrate (50 ml), pH 2.8 and equilibrated with 20 mM sodium phosphate buffer, pH 7.0, before using the resin for affinity purification.

4. Affinity Purification of Aβ-sdAb 1a

The crude mixture of sdAbs obtained after size fractionation on Superdex-200, which was more than 98% free of full-length conventional IgGs, was allowed to incubate with the affinity column in 1×PBS, at room temperature for one hour. After one hour, the unbound material was allowed to drain through the column and the column washed with PBS until all the unbound proteins had been washed off the column. The bound Aβ-sdAb was eluted off the column with pH 2.8 buffer (0.1 M sodium citrate, 0.2 um filtered). The eluant was adjusted to pH 7.2 by adding 1 M Tris.HCl, pH 9.0, and concentrated on Millipore-Amicon Ultra-15 concentrators (30 KDa molecular weight cutoff). The retentate was buffer exchanged to 1×PBS and stored at −20° C. to obtain 1.65 mg of Aβ-sdAb 1a (FIG. 2, Structure 1, Table 1, Variant: R=1). Its protein concentration was determined using Pierce's BCA Protein Assay Kit. The SDS-PAGE analysis of the affinity purified Aβ-sdAb 1a is in FIG. 3. About 10 ug of the Aβ-sdAb 1a after each step was electrophoressed on 12% SDS-PAGE gel after loading in SDS-loading buffer. The electrophoresis was performed at 100 volts for one hour, the gel was stained in 0.04% Coomassie Blue stain for 30 minutes at room temperature (RT). Coomassie blue stained SDS-PAGE (12%) protein gel of sequentially purified Aβ-sdAb 1a, panel D: $1^{st}$ and $2^{nd}$ purifications were on Supordex-200; $3^{rd}$ purification was done by affinity chromatography.

B. Synthesis of Single-Chain Aβ-SDAB 2A and Epitope Mapping of Peptide Composition 2A 1. Isolation of Single-Chain Aβ-sdAb 2a from Aβ-sdAh 1a 1.0 mg of Aβ-sd-Ab 1a was dissolved in 400 ul of pH 7.4 PBS. To this solution was added 100 ul of 190 mM triethoxy carboxyl-phospine (TCEP) in PBS to obtain a final concentration of 20 mM. The reaction mixture was incubated at 4° C. for 12-15 hours when gel electrophoresis (10% SDS-PAGE) showed a low molecular weight species with molecular weight of ~50 KDa. This product peptide composition 2a (single chain of Aβ-sdAb 1a) was isolated by gel filtration and tested by Western and ELISA.

2. Epitope Mapping of Single-Chain Aβ-sdAb 2a

96-Well microplates (A1-A12 through G1-12 wells) were coated in triplicate with 600 ng per well of the following synthetic amyloid-peptide segments of Aβ1-42 peptide in Table 7.

TABLE 7

| Synthetic amyloid-peptide segments of Aβ1-42 peptide | |
|---|---|
| Peptide segment | Amino acid positions |
| 1 | 1-16 |
| 2 | 5-20 |
| 3 | 9-24 |
| 4 | 13-28 |
| 5 | 17-32 |
| 6 | 21-37 |
| 7 | 25-41 |
| 8 | 29-42 |

After coating the plate at 4° C. for 12 hours, the antigens were discarded and the wells washed with deionized water (3×). The plate was blocked with 1% BSA in 50 mM Tris/150 mM NaCl, pH 7.5 for one hour. At the end of one hour, single-chain Aβ-sdAb, 2a, 1.0 ug diluted to 2500 ul with 1% BSA/Tris buffer was added to the top row (100 ul per well in triplicates). After serial dilution all the way to 1:320000 ul the plate was incubated with gentle shaking at room-temperature for 2 hours. At the end of 2 hour incubation, the plate was washed three times, 250 ul per well, with 0.05% tween-20/PBS. After washing, the wells were incubated with 100 ul per well of goat-anti-llama-IgG-HRP conjugate (Bethyl Labs, Texas) 1.0 ug diluted to 10 ml of 1% BSA in PBS. After one hour incubation, the plate was washed with 0.05% Tween as above. The washed well were treated with 100 ul of TMB substrate and the plate read at 370 nm. The highest antibody titer was detected with the peptide 1-16 amino acid long.

Subsequently, two synthetic-peptide were synthesized: the 1-8 and 9-16 peptides from the amyloid beta peptide and the above ELISA was again repeated with the plate coated with 600 ng of each of the peptide in triplicates. This time the peptide of the 9-16 amino acids gave the highest antibody titer, and no reaction took place with the sequence 1-8 mer. The epitope is between 9 to 16 amino acids with the following sequence: G Y E V H H Q K (SEQ ID NO: 14).

C. Synthesis of Peptide Composition Structure 2 in FIG. 2 Derivatives

1. Protease Digestion of Single-Chain Aβ-sdAb 2a to Obtain Aβ-Vab-HR (Aβ-Vab with L1 or L2 Linker Variant)

Generation of Sepharose-Endoproteinase Glu-C Conjugate.

Endoproteinase Glu-C (Worthington Biochemical Corporation), 4 mg, was conjugated to 250 mg of CNBr-activated Sepaharose (GE Healthcare, catalogue #17-0430-1) in pH 8.5 0.1 M NaHCO$_3$/0.5M NaCl in 1×10 cm long spin fitted with a medium fritted disc, as described in Section A3: Generation of an Affinity Column for Enrichment of Aβ-sdAb 1a. After conjugation, any unbound Glu-C proteinase was removed by extensive washing of Sepharose and the column was stored in 0.1% NaN$_3$/PBS until used. The Sepharose had swollen to about an 0.5 ml volume.

Digestion of Single-Chain Aβ-sdAb 2a and Isolation of Aβ-Vab-HR.

Aβ-sdAb 2a (1 mg, ~11 nmols) was dissolved in 1.0 ml of pH 7.5 0.1 M NaHCO$_3$ and added to the 0.8 ml of Sepharose-Glu-C conjugate. The reaction mixture was gently rocked on a rocker for 4 hours and the contents were collected by draining the column and washing it with 4 ml of the conjugation buffer, 0.1 M NaHCO$_3$, pH 7.5. The combined flowthrough was passed through Aβ$_{1-35}$-affinity column generated in Section A3. After washing off the unbound material, the bound Aβ-Vab-HR (HR=hinge region) from single-chain Aβ-sdAb 2a was elated with pH 2.8 0.1 M sodium citrate and the product buffer exchanged to 1×PBS, pH 7.4. It was tested by ELISA.

2. Methods for Linking Aβ-Vab-HR to Antibody Constant Domains

General Method for Expression of Engineered Human Antibody Constant Domains, CH1, CH2 and CH3. Expression of engineered human constant domains CH1, CH2 and CH3 was accomplished by buying the commercially available plasmid, pFUSE-CHIg (Invitrogen: pFUSE-CH1g-hG1 pFUSE-CHIg-hG2, or pFUSE-CBIg-hG3), and using them each for transformation of E. coli strain HB2151 cells. The cultures were grown in SB media at 37° C. until an optical density of ~0.7 was obtained. Expression was then induced with 1 mM IPTG (isopropyl-1-thio-b-D-galactopyranoside) at 37° C. for 15-16 hours. The bacterial cells were harvested and re-suspended in a culture medium containing 10% of 50 mM Tris.HCl, 450 mM NaCl, pH 8.0. Polymyxin B sulfate (PMS) was added to the culture medium, 1:1000 volume of PMS: culture volume. After centrifuging the cell lysate at 15000 RPM for 45 minutes at 4% the supernatant was purified by HiTrap Ni-NTA column and tested for the respective expressed human constant domain by SDS-PAGE and Western blot.

General Method for Native Chemical Ligation of Aβ-Vab-HR to Human Constant Domain.

For native chemical ligation (FIG. 4), an unprotected peptide-alpha-carboxy thioester (peptide 1) was reacted with a second peptide (peptide 2) containing an N-terminal cysteine residue to form a natural peptide linkage between Aβ-Vab-HR and constant domain CH1 or CH2 or CH3. Aβ-Vab-HR can be modified to be peptide 1 or peptide 2. The CH1, CH2, or CH3 domain is then modified to be the recipricol peptide 2 or peptide 1. After the reaction, the Aβ-Vab-PEG-Human CH1, CH2, or CH3 was purified by size exclusion chromatography.

General Method for Maleimido-Thiol Conjugation Chemical Linkage of Aβ-Vab-HR to Human Constant Domain.

Figure 5:
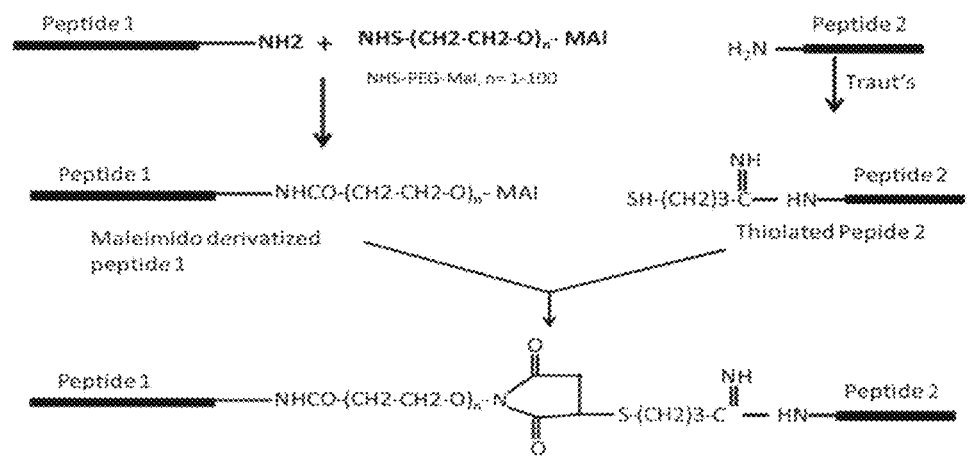
FIG. 5 depicts the synthetic sequence of conjugating two peptides by malemido and thiol groups.

For the maleimido-thiol conjugation reaction (FIG. 5), a thiolated peptide 2 conjugates to a maleimido-derivatizied peptide 1 to create aliphatic linker between Aβ-Vab-HR and a CH1, CH2, or CH3 domain. Aβ-Vab-HR can be modified to be peptide 1 or peptide 2. The CH1, CH2, or CH3 domain is then modified to be the reciprocal peptide 2 or peptide 1. Peptide 1 was converted into a maleimido peptide by reacting in with 20-fold excess of commercial NHS-PEG-Mal (MW: 3000 Da) in pH 7.0 MOPS buffer (0.1 M MOPS/0.15 M NaCl) for one hour at room temperature. After the reaction, excess PEGreagent was removed by dialysis on Vivaspin-20 column with a MWCO: 10 KDa. To generate compatible reacting group, peptide 2 was thiolated with commercial Traut's reagent to obtain thiolated peptide 2. 1.2 molar equivalent of thiolated peptide 2 which was reacted with maleimido derivatized peptide 1 at pH 6.8 at room temperature for 2 hours. After the reaction, the Aβ-Vab-PEG-Human CH1, CH2, or CH5 was purified by size exclusion chromatography.

D. Phage-Display CDNA Library Generation of Aβ-SDAB 1

1. Cloning cDNA encoding the Aβ-sdAb 1a: mRNA isolation and Reverse Transcription The isolation of total RNA from peripheral blood lymphocytes (PBLs) from 100 ml blood samples from immunized animals and subsequent reverse transcription to cDNA was done using commercial kits, such as PAXgene Blood RNA Tubes and Blood RNA Kit system (Qiagen, Mississauga, ON).

2. PCR Amplification of cDNA and Construction of Expression Vector

Amplification of cDNA was done using PCR with primers SEQ ID NO:1 and SEQ ID NO:2. The second round of PCR amplification was done using primers with built-in restriction enzyme sites (SEQ ID NO: 3 and SEQ ID NO: 4) for insertion into pHEN4 phagemid, which was used to transform bacterial cells (WK6 E. coli). The clones were sequenced by the dideoxy sequencing method. Sequences were then translated so that they can be assigned to well defined domains of the sdAb.

3. General Method for Expression and Purification of Aβ-sdAb 1

The bacterial cells containing the proper plasmids were grown, and expression of the recombinant proteins induced with 1 mM isopropyl-β-D-thiogalactopyranoside (IPTG). The periplasmic proteins were extracted by osmotic shock in the presence of protease inhibitors [(4-(2-aminoethyl) benzenesulfonyl fluoride (AEBSF) and leupeptin)], and recombinant protein purified by immobilized metal affinity chromatography (Ni-NTA Superflow, Qiagen). The MALDI-TOF mass spectrometry of Aβ-sdAb 1a in sinapinic acid displayed a molecular ion at m/e 84873.5842. The molecular weight was validated by SDS-PAGE and Western blot. The purified Aβ-sdAb 1a was further characterized by ELISA and immunohistochemical staining of tissues from transgenic mice and human patients.

4. ELISA Results for Single-Chain Aβ-sdAb 1a

Figure 4:
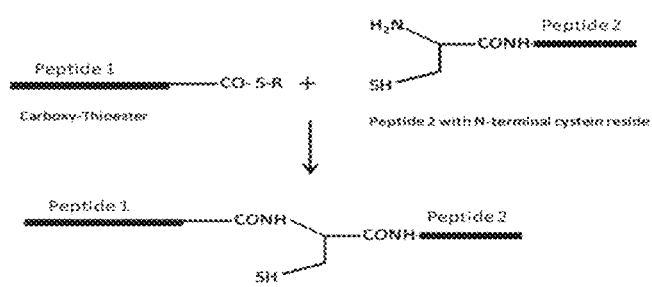
FIG. 4 depicts the synthetic sequence of conjugating two peptides by native chemical ligation.
Figure 6:
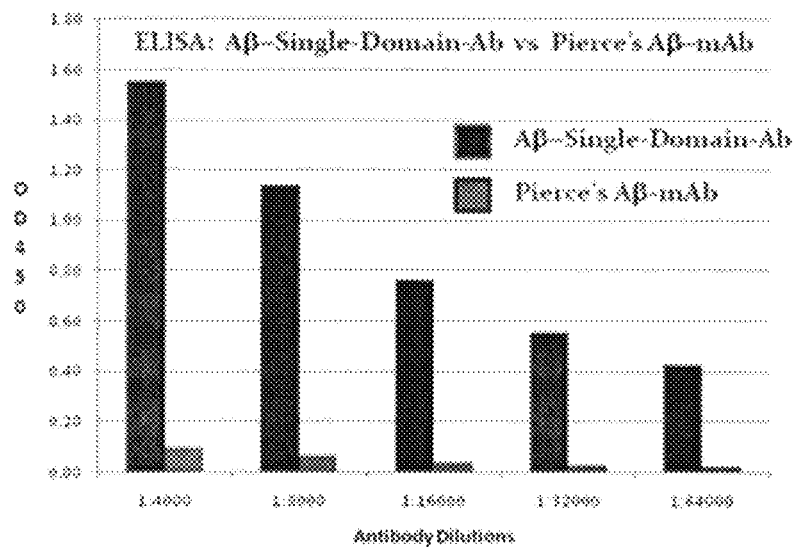
FIG. 6 is a photograph of the ELISA results of Aβ-sdAb 1a and Pierce's Aβ-mAb binding affinity to the Aβ-42 peptide as measured by the OD450 readings of the chromogenic yellow color generated by the reaction of the APP secondary antibody with the TMB substrate.

FIG. 4 depicts the results of ELISA performed in Pierce's MaxiSorp plate, which had been coated with 500 ng/well of Aβ-42 peptide at pH 9.5 overnight at room temperature. After washing the plate with water, the antigen coated wells were blocked with 1% BSA and subsequently treated with identical concentrations of Aβ-sdAb 1a and mouse-Aβ-mAb for the same length of time and temperature (2 hours at RT). Detection was done using HRP labeled secondary antibody and TMB as a substrate. The blue color generated by HRP reaction was quenched with 1.0 M HCl and OD450 recorded on Molecular Devices SpectraMax Plus plate reader. FIG. 6 is the plot of OD450 readings of the chromogenic yellow color generated by the reaction of the substrate with the MRP-enzyme. The single-domain, antibody 1a clearly outperformed the commercial Aβ-mouse-mAb.

E. Administration and Dosage.

Pharmaceutical formulations of a therapeutically effective amount of a polypeptide of the invention can be administered orally or parenterally in admixture with a pharmaceutically acceptable carrier adapted for the route of administration.

Methods well known in the an for making formulations are found, for example, in Remington's Pharmaceutical Sciences (18th edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium, stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

The amount of active polypeptide in the compositions of the invention can be varied. One skilled in the art will appreciate that the exact individual dosages may be adjusted somewhat depending upon a variety of factors, including the ingredient being administered, the time of administration, the route of administration, the nature of the formulation, the rate of excretion, the nature of the subject's conditions, and the age, weight, health, and gender of the patient. In addition, the severity of the condition targeted by an agent of the invention will also have an impact on the dosage level. Generally, dosage levels of an agent of the invention of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above-identified factors.

Methods for administering peptides to a subject are described, for example, in U.S. Pat. Nos. 5,830,851; 5,558,085; 5,916,582; 5,960,792; and 6,720,407, hereby incorporated by Reference.

F. Ex-Vivo and In-Vivo Results of Peptide Compositions 1A and 2A in Alzheimer's Disease Models 1. Detection of Amyloid Plaque in Transgenic Mouse and Human Alzheimer's Patients with Peptide Composition 2a in Ex-Vivo Experiments The specificity of Aβ-sdAb for Aβ was tested by immunohistochemical (IHC) staining of paraffin embedded brain tissues if our the APP transgenic mouse (FIG. 7A upper two frames) and Alzheimer's patient (FIG. 7A lower two frames), with and without primary Aβ-sdAb. The same tissues were stained with Thioflavin-S dye (FIG. 7B). Paraffin tissues were cut in a microtome to the thickness of 5 microns, mounted on APES coated slides, dried at room temperature (RT) for 24 hours, and then deparaffinized using xylene and ethanol. Washed slides were blocked in 10% normal serum with 1% BSA (2 hours at RT), and treated with single-chain Aβ-sdAb 2a in PBS containing 1% BSA (1:100 dilution, overnight at 4° C.). After washing slides with 0.1% Triton X-100, endogenous peroxidase activity was blocked with 0.3% hydrogen peroxide, followed by treatment with biotinylated goat-anti-llama-IgG. Detection was done with streptavidin-HRP and diaminobenzidine as HRP substrate.

2. Demonstration of BBB Permeability of Aβ-Vab Peptide Compositions 1a and 2a in Alzheimer's-Like Transgenic Mice We tested the BBB permeability of Aβ-sdAb 1a and single-chain Aβ-sdAb 2a. The single-chain Aβ-sdAb 2a had been prepared by the TCEP (triethoxy-phosphine) reduction of Aβ-sdAb 1a above in Section B.1. To demonstrate BBB penetration, 60 ug of Aβ-sdAh 1a or single-chain Aβ-sdAb 2a was injected in the tail vein (FIG. 8) of the live transgenic mice (J9 strain: PDGF-APP-SW-Ind; APP: amyloid precursor protein; SW and Ind stand for Swedish and Indiana mutations in APP), according to the protocol outlined below (Table 8). The commercial mouse-Aβ-mAb was also used for comparative purposes. Non-transgenic mice were used as negative controls.

TABLE 8

Protocol for Demonstrating BBB Permeability

| Group | Mouse | Antibody | Time | Number of mice |
|---|---|---|---|---|
| 1 | APP tg mice | ICBI-antibody | 4 h | 6 |
| 2 | APP tg mice | ICBI-antibody | 24 h | 6 |
| 3 | APP tg mice | Mouse-Ab-IgG | 4 h | 6 |
| 4 | APP tg mice | Mouse-Ab-IgG | 24 h | 6 |
| 5 | Non-tg control mice | ICBI-antibody | 4 h | 3 |
| 6 | Non-tg control mice | ICBI-antibody | 24 h | 3 |
| 7 | Non-tg control mice | Mouse-Ab-IgG | 4 h | 3 |
| 8 | Non-tg control mice | Mouse-Ab-IgG | 24 h | 3 |

APP = Amyloid precurson protein.
Route = Tail vein,
Dose = 60 ug,
Treatment and duration = variable.

Mice were sacrificed 4 hours and 24 hours after the injection and their brains serially sectioned. The two hemispheres were separated; the left hemisphere was rapidly snap frozen on dry ice (2 to 5 min) and stored at −80° C.; the right hemisphere was immersed in a cold 4% paraformaldehyde fixative solution.

3. Neuropathological Analysis

Figure 9:
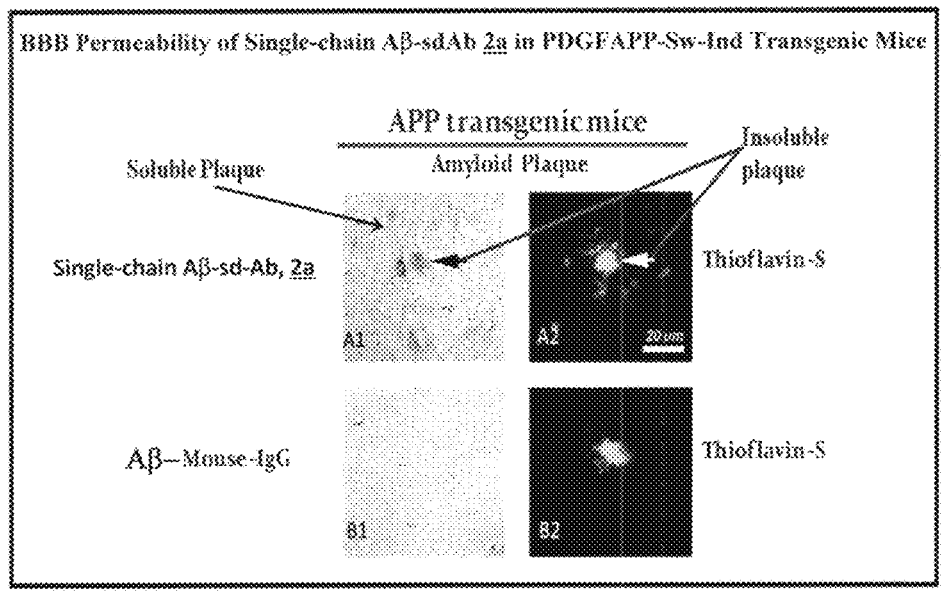
FIG. 9 is photographs of the immunostaining results from, blood-brain barrier (BBB) permeability studies, of peptide composition 2a compared to Aβ-Mouse-IgG In the live APP transgenic mice injected in their tails with peptide composition 2a or Aβ-Mouse-IgG.

The fixed half brain was serially sectioned sagitally with the vibratome at 40 um and stored at −20° C. in cryoprotective medium. Sections were immunostained with biotinylated anti-llama-IgG1 and detected with streptavidin-HRP using an enzyme substrate, followed by imaging with the laser confocal microscope (FIG. 9). Co-localization studies between llama IgG and Aβ-protein were also performed by staining the tissues with Thioflavin-S dye. Digital images were analyzed with the ImageQuant program to assess numbers of lesions.

4. Results of Blood-Brain Permeability of Peptide Compositions

All six transgenic mice analyzed 24 hours after a single low dose injection of 60 ug amyloid sd-antibody displayed labeling of amyloid-plaque in their central nervous system. The data shown in FIG. 9 represents data obtained only with single-chain Aβ-sdAb 2a. Binding of peptide compositions 1a and 2a to amyloid plaque was only detected in the APP transgenic mice, not in non-transgenic mice. More importantly, Aβ-sd-antibodies 1a and 2a labeled both the soluble/diffusible plaque and insoluble plaque, while Thioflavin-S dye labeled primarily the insoluble plaque. Soluble plaque is the one responsible for cognitive decline from Alzheimer's Disease, not the insoluble plaque, which is labeled by other neuroimaging agents such as Pittsburgh Compound B and $^{18}$F-Flutemetmol. The single-chain sdAb 2a stained about 10% of all the soluble and insoluble plaque in the mouse brain, while Aβ-sdAb 1a labeled about 3.6% of the total plaque in the same amount of time.

Figure 10:
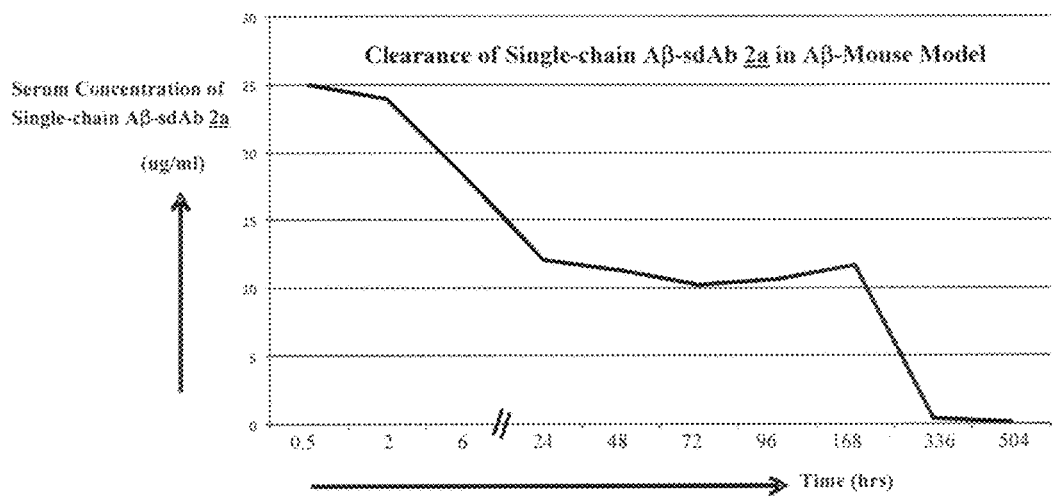
FIG. 10 is a graph of the serum retention time of the peptide composition 2a in Aβ-mice.

5. Pharmacokinetics Study of Single-Chain Aβ-sdAb 2a for Alzheimer's Disease in Mice A pharmacokinetics (PK) study of the single-chain Aβ-sdAb 2a was conducted in collaboration with Biotox Sciences, San Diego. In this study, three groups of mice (average weight: ~25 g) were infected in the tail vein with 60 ug of single-chain Aβ-sdAb 2a in 200 ul of PBS buffer. At a predetermined timepoint, blood was drawn from the animals the the serum was analyzed for the concentration of the single-chain Aβ-sdAb 2a by ELISA. All three-sets of animals showed identical clearance of the single-chain Aβ-sdAb 2a from the blood (FIG. 10). FIG. 10 is a graph of the serum mention time of the single-chain Aβ-sdAb 2a in Aβ-mice. The X-axis represents time in hours and the Y-axis concentration of single-chain Aβ-sdAb 2a per ml of serum. The two broken lines indicate non-linearity in the X-axis. Clearance of amyloid-plaque by binding to mouse-Aβ-mAb and subsequent phagocytosis has been reported in the literature [Wang, Y-J, et al., Clearance of amyloid-beta in Alzheimer's disease: progress, problems and perspectives, *Drug Discovery Today*, 11, 931 (2006)].

Although at 24 h the serum concentration of 2a in FIG. 10 dropped to about half compared to what it was at 0.5 hour, its levels stayed at ~40% for 7 days, suggesting that the single-chain Aβ-sdAb 1a has a serum life of at least 7 days and, therefore, a remarkable potential for developing diagnostic and long-acting therapeutic agents. The slow decrease in serum concentrations of the single-chain Aβ-sdAb 2a in the first 24 h could be attributed to its binding with the amyloid-peptide.

G. Synthesis of Antibody-Coated Nano-Particles with Peptide Compositions 1 and 2 from FIG. 2

1. Synthesis of Polybuytcyanoacrylate (PBCA) Nanoparticles 5

Figure 2:
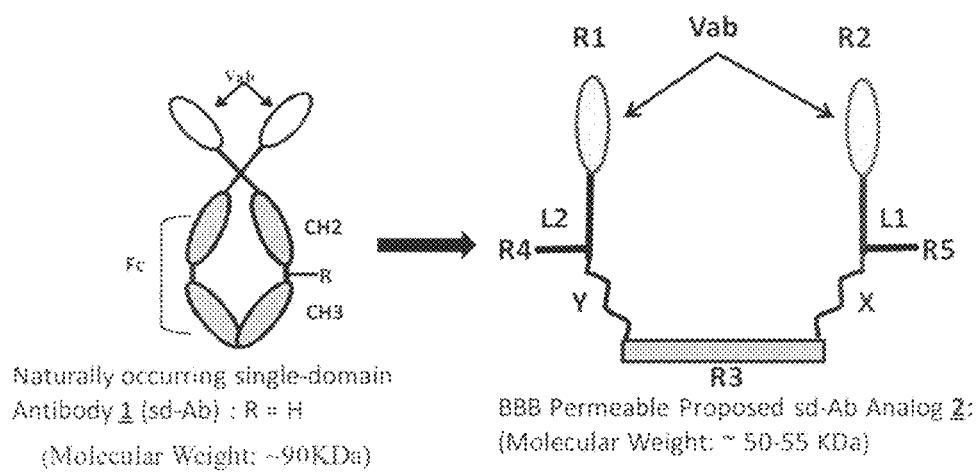
FIG. 2 depicts generic blood-brain permeable peptide composition structures 1 and 2 where each structure contains at least one Vab domain and each Vab domain was derived from a camelid Vab, shark V-NAR, or a combination thereof, from one or more sdAbs for an antigen.
Figure 3:
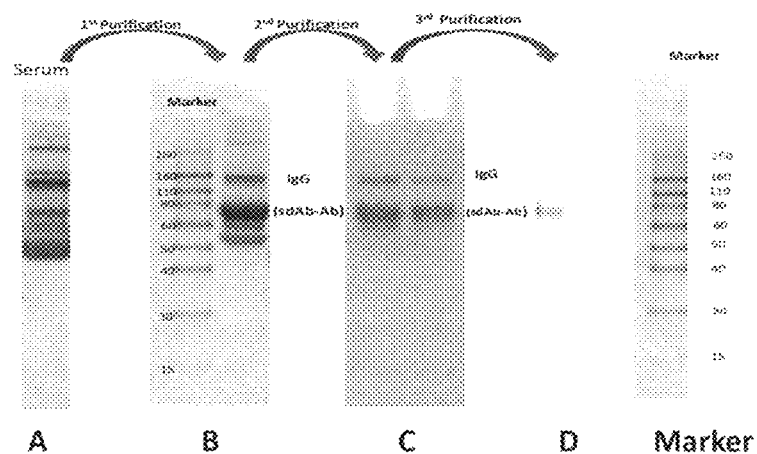
FIG. 3 is a photograph of affinity-purified Aβ-sdAb 1a on an SDS-PAGE gel.
Figure 11:
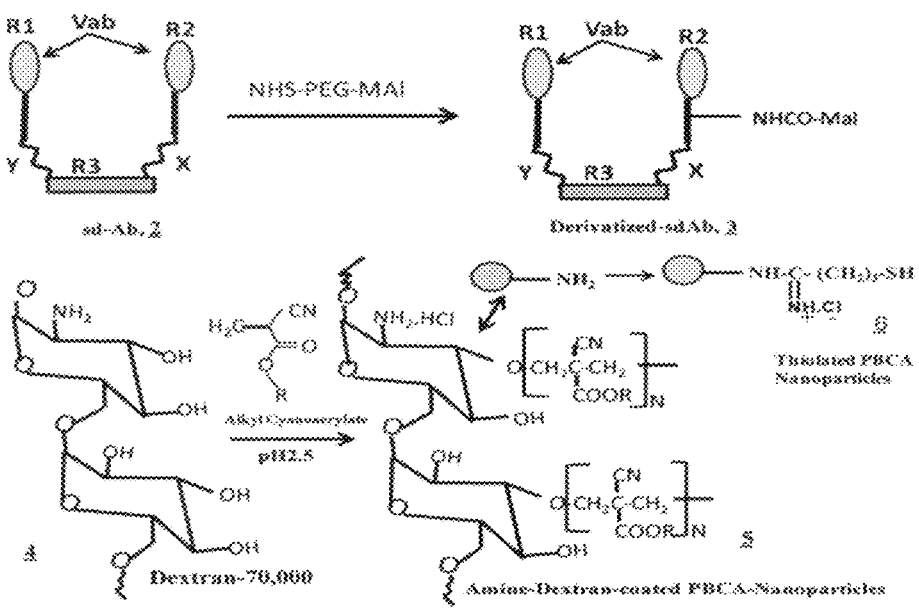
FIG. 11 depicts the generic synthetic sequence of synthesizing maleimido derivatized peptide composition 3 from peptide composition 2 (structure 2 in FIG. 2) and synthesizing thiolated dextran-PBCA-nanoparticles 6 from dextran 4.
Figure 12:
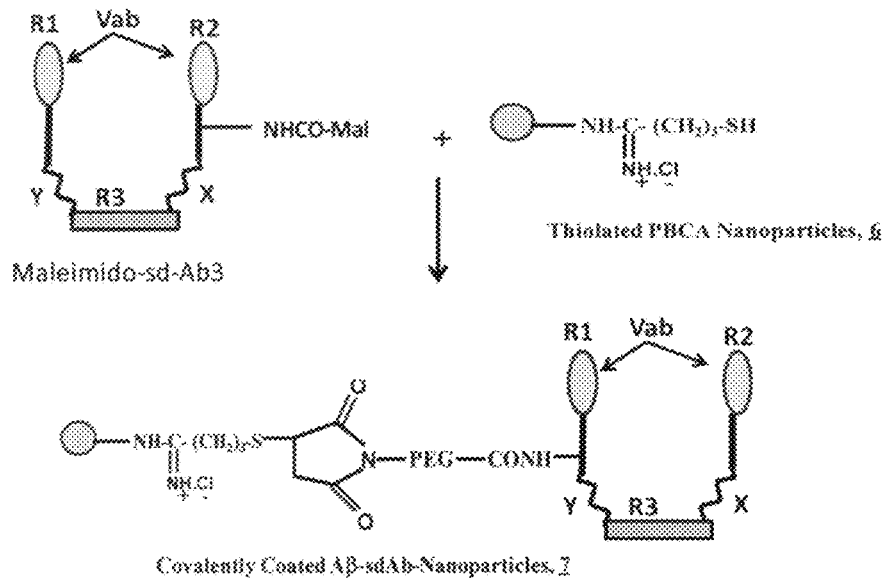
FIG. 12 depicts the generic conjugation, after the sequence in FIG. 11, of maleimido-peptide composition 3 to thiol-functionalized dextran-coated PBCA-nanoparticles 6, forming covalently-coated peptide composition 2-nanoparticle 7.
Figure 13:
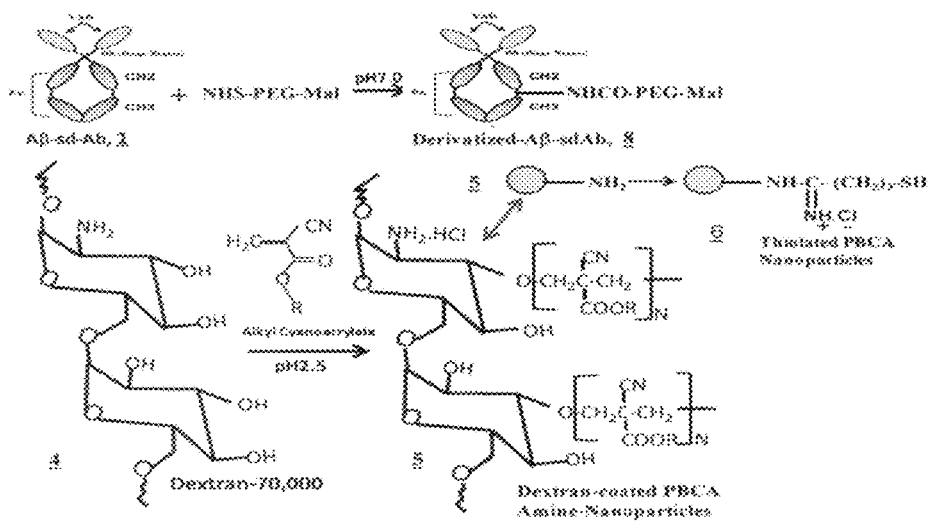
FIG. 13 depicts the generic synthetic sequence of synthesizing maleimido derivitized-sdAb 8 from sd-Ab 1 (Structure 1 in FIG. 2) and synthesizing thiolated dextran-PBCA-nanoparticles 6 from dextran 4.

To overcome the shortcomings of the prior art, this invention describes the synthesis of biodegradable polyalkylcyanoacrylate nanoparticles coated with aminated dextran and peptide compositions 1 and 2 in FIG. 2. The synthetic steps are outlined in FIGS. 11-14. To a stirring solution of aminated dextran 4 (1.0 gm) in 100 ml of 10 mM HCl (pH 2.5) was slowly added 1 ml of butylcyanoacrylate (BCA) (FIG. 11 and FIG. 13). The reaction mixture was allowed to stir at RT for 4 hours to obtain a white colloidal suspension, which was carefully neutralized with 0.1 M NaHCO$_3$ solution to pH 7.0. This colloidal suspension was filtered through 100 um glass-fiber filter to remove large particles. The filtrate was spilt into 50 ml centrifuge tubes and spun at 10,000 RPM for 45 minutes. After discarding the supernatant, the particles were washed several times with deionized water, centrifuging the particles and discarding the supernatant until no more white residue was seen in the supernatant. The resulting PBCA particles, 5, were stored in 0.01% NaN$_3$/PBS at 4° C. (FIG. 11 and FIG. 13).

2. Synthesis of Thiolated PBCA Nanoparticles 6

PBCA panicles 5 were washed with 50 mM MOPS buffer, pH 7.0, to remove NaN$_3$. The particles were then treated 50 mM Traut's reagent in MOPS buffer for one hour to synthesize thiolated PBCA nanoparticles 6 (FIG. 11 and FIG. 13). The particles were then repeatedly washed to remove the unreacted Traut's reagent.

3. Synthesis of Peptide Composition Maleimido Derivatives 3 and 8

Purified peptide composition 1a (1 mg, 12.5 nM) was dissolved in 50 mM MOPS buffer, pH 7.0. It was treated with NHS-PEG-Mal (MW; 3000 Da) (250 nM) at RT for 1 hour (FIG. 12). The reaction was concentrated on Amicon-Centricon Concentrators (MW Cutoff: 30 KDa) to remove hydrolyzed and unconjugated excess NHS-PEG-Mal. The purified pegylated derivative 8 was characterized by MALDI-MS and 12% SDS-PAGE gel. A similar process can be used to convert peptide composition 2 in FIG. 2 into the pegylated derivative 3 (FIG. 11).

4. Synthesis of Covalently Conjugated Peptide Composition Nanoparticles 7 and 9

Figure 14:
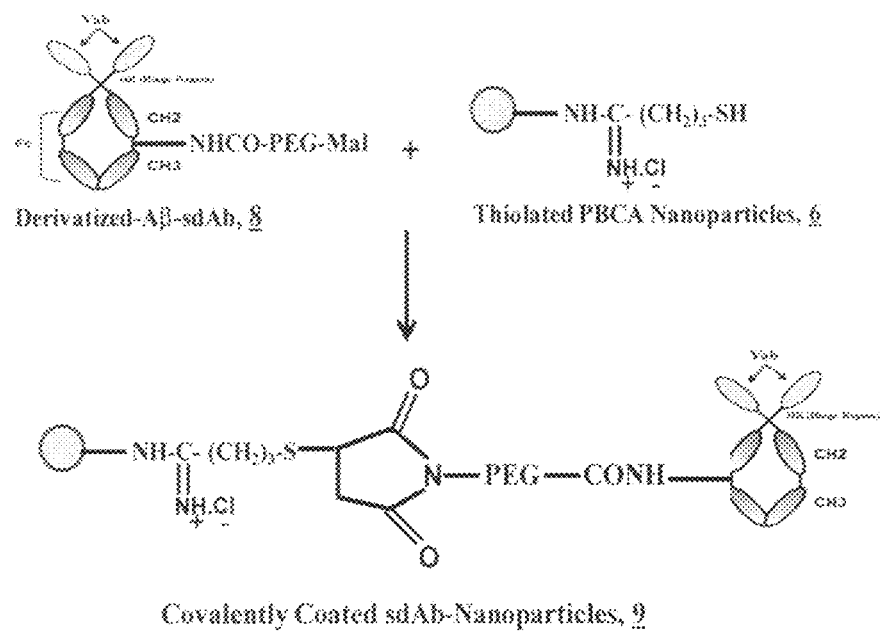
FIG. 14 depicts the generic conjugation, after the sequence in FIG. 13, of maleimido-sdAb 8 to thiol-functionalized dextran-coated PBCA-nanoparticles 6, forming covalently-coated sdAb-nanoparticle 9.
Figure 15:
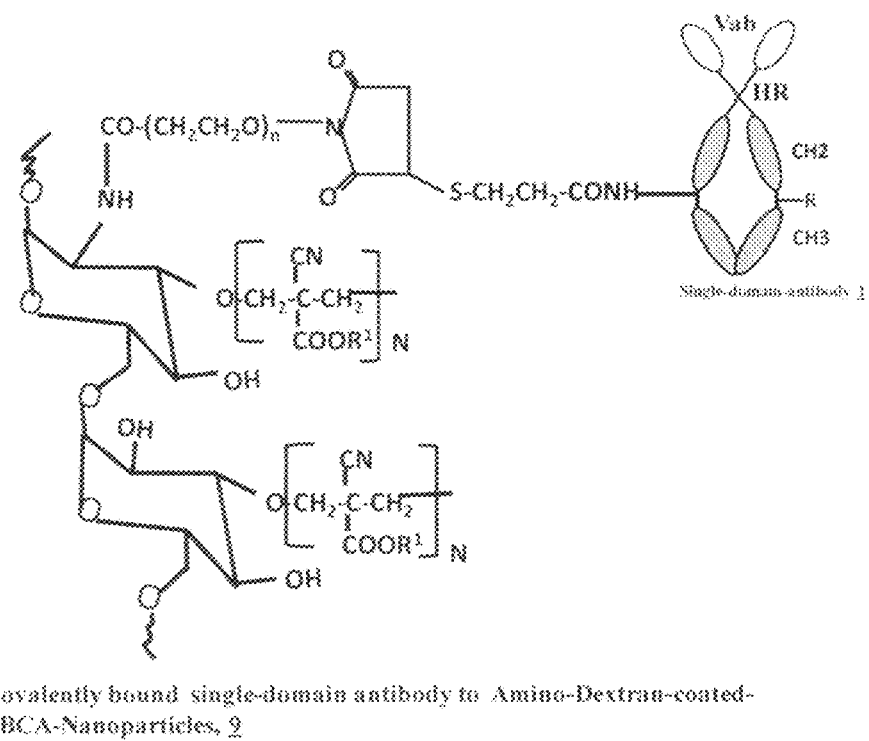
FIG. 15 is a structure of covalently-coated sdAb-nanoparticle 9 (structure 1 in FIG. 2) that is comprised of a maleimodio linker to form covalently-coated sdAb-nanoparticle 9 conjugated to an amino-dextran-coated-PBCA-nanoparticle 6.
Figure 16:
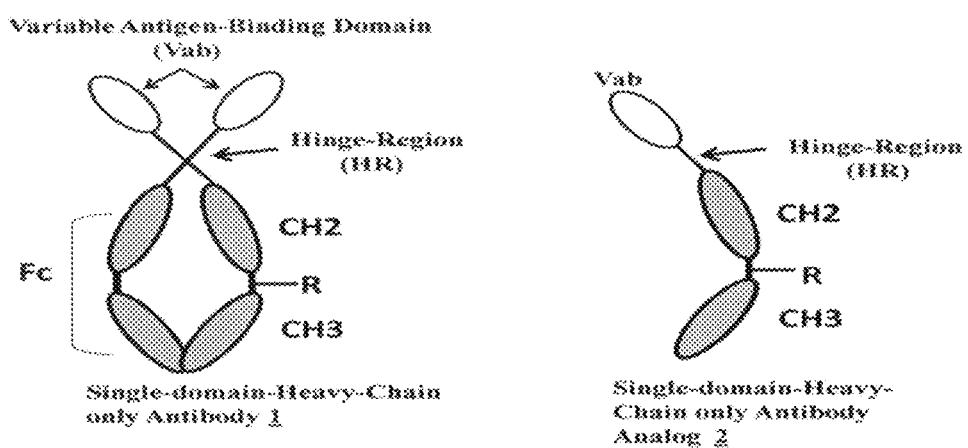
FIG. 16 illustrates the structures of a native camelid heavy chain-only antibody (left) which is a dimer formed by intermolecular bonding of two monomeric units (right), wherein R=H. Each monomer comprises the following structure: Vab-hinge region (HR)-CH2-CH3

The conjugation of maleimido-Aβ-sdAb 8 with thiolated PBCA nanoparticles 6 was carried out at pH 7.0 in 50 mM MOPS buffer in the presence of 5 mM EDTA for 4 hours at RT (FIG. 14). The resulting PBCA nanoparticles 9 were purified by washing off (5×50 ml deionized water) the unreacted maleimido antibody 3. The particles were stored in deionized water at 4° C. until used. A similar process can be used to convert pegylated derivative 3 and thiolated PBCA nanoparticles 6 into PBCA nanoparticles 7 (FIG. 12).

The present disclosure is not to be limited in terms of the particular embodiments described in this application. Many modifications and variations can be made without departing from its spirit and scope, as will be apparent to those skilled in the art. Functionally equivalent methods, processes and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, alone with the full scope of equivalents to which such claims are entitled. It is to be understood that this disclosure is not limited to particular methods, processes, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each, individual publication, patent application, issued patent or other document was specifically and individually indicated to be incorporated by reference in its entirety. Definitions that are contained in text incorporated by reference are excluded to the extent that they contradict definitions in this disclosure.

While certain embodiments have been illustrated and described, it should be understood that changes and modifications could be made therein in accordance with ordinary skill in the art without departing from the technology in its broader aspects as defined in the following claims.

What is claimed is:

1. A method for assessing an amyloid-beta peptide in the central nervous system of a subject, the method comprising:
   (i) administering to the subject a polypeptide comprising the formula:

Vab1-L1-X-R3-Y-L2-Vab2, wherein Vab1 and Vab2 each independently comprises a variable antigen-binding (Vab) domain that is derived from a camelid single domain heavy chain antibody, and at least one of the variable antigen binding domains comprises amino acids 1-127 of the amino acid sequence of SEQ ID NO: 11 and is capable of binding to an amyloid-beta peptide;
   wherein L1 and L2 each comprise a hinge region from a camelid single domain heavy chain antibody; and
   wherein the L1, L2, or both further comprise a covalently-attached-detectable label,
   wherein the detectable label comprises a nanoparticle that comprises polybutylcyanoacrylate and dextran;
   wherein X and Y are bifunctional linkers, wherein X and Y are selected from the group consisting of —NHCO—$(CH_2CH_2O)_n$— and wherein n=2-100, —CH$(CH_2SH)$—NHCO, —$(C_4H_3NO_2)$—S—$(CH_2)_3$-imidate-, and —NHCO—$(CH_2CH_2O)_n$—$(C_4H_3NO_2)$—S—$(CH_2)_3$-imidate- and wherein n=2-100;
   wherein R3 comprises at least one constant domain of human IgG CH2 or CH 3 domain, and
   wherein the polypeptide is capable of specifically binding to an amyloid-beta peptide within the central nervous system (CNS) of the subject;
   (ii) waiting for a time sufficient for the polypeptide to permeate the blood-brain-barrier of the subject and bind to the amyloid-beta peptide; and
   (iii) detecting the presence or amount of the detectable label within the CNS of the subject.

2. The method of claim 1, wherein X comprises —NHCO—$(CH_2CH_2O)_n$—$(C_4H_3NO_2)$—S—$(CH_2)_3$-imidate- and wherein n=2-100.

3. The method of claim 1, wherein Y comprises —NHCO—$(CH_2CH_2O)_n$—$(C_4H_3NO_2)$—S—$(CH_2)_3$-imidate- and wherein n=2-100.

4. The method of claim 1, wherein X, Y, or both comprise NHCO—.

5. The method of claim 1, wherein the detectable label is covalently attached through an NHS-PEG-Mal linker.

6. The method of claim 1, wherein the detectable label is a radioisotope, a fluorophores, a toxin, biotin, digoxigenin, avidin, or streptavidin.

7. The method of claim 1, wherein the detectable label comprises a nanoparticle having a diameter of about 10 nm to about 500 nm.

8. The method of claim 1, wherein the nanoparticle is covalently linked to at least one of L1 and L2 via a linker comprising —NHCO—.

9. The method of claim 1, wherein the hinge region corresponds to the amino acid sequence of SEQ ID NO: 13.

10. The method of claim 1, wherein the detectable label comprises a nanoparticle that is covalently attached to at least one of L1 and L2 through an NHS-PEG-Mal.

* * * * *

```
                              SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caggttcagc ttgttgcttc tggt                                             24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttaccagga gaaagagaaa g                                                21

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgagcagg ttcagcttgt tgcttctggt                                       30

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggccgctt taccaggaga aagagaaag                                        29

<210> SEQ ID NO 5
```

<211> LENGTH: 1131
<212> TYPE: DNA
<213> ORGANISM: Unknown
<220> FEATURE:
<223> OTHER INFORMATION: Description of Unknown: Camelid heavy-chain of single-domain antibody polynucleotide

<400> SEQUENCE: 5

| | | |
|---|---|---|
| caggttcagc ttgttgcttc tggtggtggc tctgttcagg ctggtggttc tcttcgtctt | 60 |
| tcttgtgctg cttctggtta tactttttct tcttatccta tgggttggta tcgtggtgct | 120 |
| cctggtaaag aatgtgaact ttctgctcgt attttttctg atggttctgc taattatgct | 180 |
| gattctgtta aaggtcgttt tactatttct cgtgataatg ctgctaatac tgcttatctt | 240 |
| ggtatggatt ctcttaaacc tgaagatact gctgtttatt attgtgctgc tggtcctggt | 300 |
| tctggtaaac ttgttgttgc tggtcgtact tgttatggtc ctaattattg gggtggcggt | 360 |
| actcaggtta ctgtttcttc tgaacctaaa attcctcagc tcagcctaa acctcagcct | 420 |
| cagcctcagc tcagcctaa acctcagcct aaacctgaac tgaatgtac ttgtcctaaa | 480 |
| tgccctgctc ctcctgttgc cggcccttct gttttctttt tcctcctaa acctaaagat | 540 |
| actcttatga tttctcgtac tcctgaagtt acttgtgttg ttgttgatgt ttctcatgaa | 600 |
| gatcctgaag ttcagtttaa ttggtatgtt gatggtgttg aagttcataa tgccaaaact | 660 |
| aaacctcgtg aagaacagtt taattctact tttcgtgttg tttctgttct tactgttgtt | 720 |
| catcaggatt ggcttaatgg taagaatat aaatgtaaag tttctaataa aggtcttcct | 780 |
| gctcctattg aaaaaactat ttctaaaact aaaggccagc ctcgtgaacc tcaggtttat | 840 |
| actcttcctc cttctcgtga agaaatgact aaaaatcagg tttctcttac ttgtcttgtt | 900 |
| aaaggttttt atccttctga tattgttgaa tgggaatcta atggccagcc tgaaaataat | 960 |
| tataaaacta ctcctcctat gcttgattct gatggttctt tttttcttta ttctaaactt | 1020 |
| actgttgata atctcgttg gcagcagggt aatgttttt cttgttctgt tatgcatgaa | 1080 |
| gctcttcata atcattatac tcagaaatct ctttctcttt ctcctggtaa a | 1131 |

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 36
<212> TYPE: PRT
<213> ORGANISM: Homo sapiens

<400> SEQUENCE: 7

Asp Ala Glu Phe His Arg Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Cys

<210> SEQ ID NO 8
<211> LENGTH: 17
<212> TYPE: PRT
<213> ORGANISM: Homo sapiens

<400> SEQUENCE: 8

Cys Asp Ala Glu Phe His Arg Asp Ser Gly Tyr Glu Val His His Gln
1               5                   10                  15

Lys

<210> SEQ ID NO 9
<211> LENGTH: 15
<212> TYPE: PRT
<213> ORGANISM: Homo sapiens

<400> SEQUENCE: 9

Cys Glu Asp Val Gly Ser Asn Lys Gly Ala Ile Ile Gly Leu Met
1               5                   10                  15

<210> SEQ ID NO 10
<211> LENGTH: 16
<212> TYPE: PRT
<213> ORGANISM: Homo sapiens

<400> SEQUENCE: 10

Asp Ala Glu Phe His Arg Asp Ser Gly Tyr Glu Val His His Gln Lys
1               5                   10                  15

<210> SEQ ID NO 11
<211> LENGTH: 378
<212> TYPE: PRT
<213> ORGANISM: Unknown
<220> FEATURE:
<223> OTHER INFORMATION: Description of Unknown: Camelid single-domain
      heavy-chain antibody polypeptide

<400> SEQUENCE: 11

Gln Val Gln Leu Val Ala Ser Gly Gly Gly Ser Val Gln Ala Gly Gly
1               5                   10                  15

Ser Leu Arg Leu Ser Cys Ala Ala Ser Gly Tyr Thr Phe Ser Ser Tyr
                20                  25                  30

Pro Met Gly Trp Tyr Arg Gly Ala Pro Gly Lys Glu Cys Glu Leu Ser
            35                  40                  45

Ala Arg Ile Phe Ser Asp Gly Ser Ala Asn Tyr Ala Asp Ser Val Lys
        50                  55                  60

Gly Arg Phe Thr Ile Ser Arg Asp Asn Ala Ala Asn Thr Ala Tyr Leu
65                  70                  75                  80

Gly Met Asp Ser Leu Lys Pro Glu Asp Thr Ala Asp Tyr Tyr Cys Ala
                85                  90                  95

Ala Gly Pro Gly Ser Gly Lys Leu Val Val Ala Gly Arg Thr Cys Tyr
            100                 105                 110

Gly Pro Asn Tyr Trp Gly Gly Gly Thr Gln Val Thr Val Ser Ser Glu
        115                 120                 125

Pro Lys Ile Pro Gln Pro Gln Pro Lys Pro Gln Pro Gln Pro Gln Pro
    130                 135                 140

Gln Pro Lys Pro Gln Pro Lys Pro Glu Pro Glu Cys Thr Cys Pro Lys
145                 150                 155                 160

Cys Pro Ala Pro Pro Val Ala Gly Pro Ser Val Phe Leu Phe Pro Pro

```
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Gln Phe Asn Trp
            195                 200                 205

Tyr Val Asp Gly Val Glu Val His Asn Ala Lys Thr Lys Pro Arg Glu
            210                 215                 220

Glu Gln Phe Asn Ser Thr Phe Arg Val Val Ser Val Leu Thr Val Val
225                 230                 235                 240

His Gln Asp Trp Leu Asn Gly Lys Glu Tyr Lys Cys Lys Val Ser Asn
            245                 250                 255

Lys Gly Leu Pro Ala Pro Ile Glu Lys Thr Ile Ser Lys Thr Lys Gly
            260                 265                 270

Gln Pro Arg Glu Pro Gln Val Tyr Thr Leu Pro Pro Ser Arg Glu Glu
            275                 280                 285

Met Thr Lys Asn Gln Val Ser Leu Thr Cys Leu Val Lys Gly Phe Tyr
            290                 295                 300

Pro Ser Asp Ile Ser Val Glu Trp Glu Ser Asn Gly Gln Pro Glu Asn
305                 310                 315                 320

Asn Tyr Lys Thr Thr Pro Pro Met Leu Asp Ser Asp Gly Ser Phe Phe
            325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
            355                 360                 365

Gln Lys Ser Leu Ser Leu Ser Pro Gly Lys
            370                 375

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Tyr Gly Gly Arg
1               5

<210> SEQ ID NO 13
<211> LENGTH: 35
<212> TYPE: PRT
<213> ORGANISM: Unknown
<220> FEATURE:
<223> OTHER INFORMATION: Description of Unknown: Camelid single-domain
      heavy-chain antibody hinge-region polypeptide

<400> SEQUENCE: 13

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
            20                  25                  30

Lys Cys Pro
        35

<210> SEQ ID NO 14
<211> LENGTH: 8
<212> TYPE: PRT
```

```
<213> ORGANISM: Homo sapiens

<400> SEQUENCE: 14

Gly Tyr Glu Val His His Gln Lys
1               5
```